(12) United States Patent
Luedicke et al.

(10) Patent No.: US 11,630,106 B2
(45) Date of Patent: Apr. 18, 2023

(54) DIAGNOSTIC TEST FOR DISTINGUISHING THE SMOKING STATUS OF A SUBJECT

(71) Applicant: PHILIP MORRIS PRODUCTS S.A., Neuchatel (CH)

(72) Inventors: Frank Luedicke, Evilard (CH); Manuel C. Peitsch, Peseux (CH)

(73) Assignee: Philip Morris Products S.A., Neuchatel (CH)

( * ) Notice: Subject to any disclaimer, the term of this patent is extended or adjusted under 35 U.S.C. 154(b) by 402 days.

(21) Appl. No.: 16/495,669

(22) PCT Filed: May 18, 2018

(86) PCT No.: PCT/EP2018/063228
§ 371 (c)(1),
(2) Date: Sep. 19, 2019

(87) PCT Pub. No.: WO2018/211126
PCT Pub. Date: Nov. 22, 2018

(65) Prior Publication Data
US 2020/0141933 A1    May 7, 2020

(30) Foreign Application Priority Data
May 19, 2017 (EP) .................................... 17172100

(51) Int. Cl.
*G01N 33/543* (2006.01)
*G01N 21/77* (2006.01)
*G01N 33/94* (2006.01)

(52) U.S. Cl.
CPC ....... *G01N 33/54386* (2013.01); *G01N 21/77* (2013.01); *G01N 33/94* (2013.01); *G01N 2021/775* (2013.01)

(58) Field of Classification Search
CPC .. G01N 33/54386; G01N 21/77; G01N 33/94; G01N 2021/775; G01N 33/558;
(Continued)

(56) References Cited

U.S. PATENT DOCUMENTS 4,775,636 A   10/1988  Moeremans
4,816,567 A    3/1989  Cabilly
(Continued)

FOREIGN PATENT DOCUMENTS

CN    102033127    4/2011
CN    106053788   10/2016
(Continued)

OTHER PUBLICATIONS

Minet et al., "Urinary excretion of the acrylonitrile metabolite 2-cyanoethylmercapturic acid is correlated with a variety of biomarkers of tobacco smoke exposure and consumption", 2011, Biomarkers, 16(1): 89-96 (Year: 2011).*
(Continued)

*Primary Examiner* — Melanie Brown
*Assistant Examiner* — Jennifer H. Tieu
(74) *Attorney, Agent, or Firm* — Mueting Raasch Group

(57) ABSTRACT

There is disclosed herein a device for determining the smoking status of a subject, wherein said device comprises a plurality of different specific binding molecules deposited to a solid phase to detect specifically the presence of two or three tobacco smoke exposure biomarkers in a biological sample, said biomarkers consisting of: (i) cotinine and total 4-(methylnitrosamino)-1-(3-, pyridyl)-1-butanol (NNAL); (ii) cotinine and N-acetyl-S-[2-carboxyethyl]-L-cysteine (CEMA); or (iii) cotinine and NNAL and CEMA.

15 Claims, 6 Drawing Sheets

(58) Field of Classification Search
CPC ....... G01N 33/54387; G01N 33/54388; G01N 33/53; G01N 33/50
See application file for complete search history.

(56) References Cited

U.S. PATENT DOCUMENTS

| | | | |
|---|---|---|---|
| 4,853,335 A | 8/1989 | Olsen | |
| 4,859,612 A | 8/1989 | Cole | |
| 5,079,172 A | 1/1992 | Hari | |
| 5,108,889 A | 4/1992 | Smith | |
| 5,141,850 A | 8/1992 | Cole | |
| 5,202,267 A | 4/1993 | Ditlow | |
| 5,270,163 A | 12/1993 | Gold | |
| 5,514,602 A | 5/1996 | Brooks, Jr. | |
| 5,578,577 A | 11/1996 | Ching | |
| 5,616,467 A | 4/1997 | Olsen | |
| 5,681,775 A | 10/1997 | Pogge | |
| 5,726,010 A | 3/1998 | Clark | |
| 5,780,051 A | 7/1998 | Eswara | |
| 5,824,268 A | 10/1998 | Bernstein | |
| 5,965,458 A | 1/1999 | Kouonen | |
| 6,001,658 A | 12/1999 | Fredrickson | |
| 6,027,944 A | 2/2000 | Robinson | |
| 6,087,185 A | 7/2000 | Lee-Own | |
| 6,107,045 A | 8/2000 | Koren | |
| 6,194,221 B1 | 2/2001 | Rehg | |
| 6,221,625 B1 | 4/2001 | Ashibara | |
| 6,365,417 B1 | 4/2002 | Fleming | |
| 6,472,222 B2 | 10/2002 | Horst | |
| 6,482,156 B2 | 11/2002 | Iliff | |
| 6,511,814 B1 | 1/2003 | Carpenter | |
| 6,627,459 B1 | 9/2003 | Tung | |
| 6,699,722 B2 | 3/2004 | Bauer | |
| 6,706,539 B2 | 3/2004 | Nelson | |
| 6,916,666 B1 | 7/2005 | Mendel-Hartvig | |
| 6,974,706 B1 | 12/2005 | Melker | |
| 7,270,970 B2 | 9/2007 | Anderson | |
| 7,439,079 B2 | 10/2008 | Song | |
| 7,763,454 B2 | 7/2010 | Nazareth | |
| 7,775,899 B1 | 8/2010 | Cannon | |
| 7,815,854 B2 | 10/2010 | Cohen | |
| 7,816,122 B2 | 10/2010 | Clark | |
| 7,943,395 B2 | 5/2011 | Wei | |
| 8,008,448 B2 | 8/2011 | Park | |
| 8,124,421 B2 | 2/2012 | Feaster | |
| 8,137,985 B2 | 3/2012 | Song | |
| 8,173,380 B2 | 5/2012 | Yang | |
| 8,313,955 B2 | 11/2012 | Wu | |
| 8,377,379 B2 | 2/2013 | Feaster | |
| 8,679,457 B2 | 3/2014 | Alexander | |
| 8,722,426 B2 | 5/2014 | Lambotte | |
| 9,063,137 B2 | 6/2015 | Saul | |
| 9,261,522 B2 | 2/2016 | Hill | |
| 2002/0015663 A1 | 2/2002 | Goldstein | |
| 2003/0109067 A1 | 6/2003 | Brown | |
| 2005/0043515 A1* | 2/2005 | Brown | C07K 16/16 530/387.1 |
| 2005/0130120 A1* | 6/2005 | Lambotte | C12Q 1/701 435/7.1 |
| 2006/0019406 A1 | 1/2006 | Wei | |
| 2006/0068500 A1 | 3/2006 | Wei | |
| 2008/0090305 A1 | 4/2008 | Day | |
| 2013/0034866 A1 | 2/2013 | Coleman | |
| 2013/0102003 A1 | 4/2013 | Gibbs | |
| 2013/0316926 A1 | 11/2013 | Caffrey | |
| 2014/0072959 A1 | 3/2014 | Determan | |
| 2014/0073062 A1 | 3/2014 | Tamura | |
| 2015/0168397 A1 | 6/2015 | Stankov | |
| 2016/0054279 A1 | 2/2016 | Schlosser | |

FOREIGN PATENT DOCUMENTS

| | | |
|---|---|---|
| EP | 888552 | 1/1999 |
| EP | 916950 | 5/1999 |
| EP | 1657550 | 5/2006 |
| EP | 1696236 | 8/2006 |
| EP | 2047261 | 4/2009 |
| EP | 1866644 | 10/2015 |
| JP | 2012-215420 | 11/2012 |
| JP | 2014-055794 | 3/2014 |
| RU | 2593787 | 8/2016 |
| WO | WO 1998/023958 | 6/1998 |
| WO | WO 1998/036278 | 8/1998 |
| WO | WO 1998/039657 | 9/1998 |
| WO | WO 1999/013907 | 3/1999 |
| WO | WO 2000/015020 | 3/2000 |
| WO | WO 2004/027424 | 4/2004 |
| WO | WO 2005/009116 | 2/2005 |
| WO | WO 2005/039381 | 5/2005 |
| WO | WO 2005/063962 | 7/2005 |
| WO | WO 2006/009527 | 1/2006 |
| WO | WO 2006/131749 | 12/2006 |
| WO | WO 2007/023372 | 3/2007 |
| WO | WO 2007/110605 | 10/2007 |
| WO | WO 2008/030546 | 3/2008 |
| WO | WO 2009/010296 | 1/2009 |
| WO | WO 2009/136182 | 11/2009 |
| WO | WO 2010/091897 | 8/2010 |
| WO | WO 2011/061944 | 5/2011 |
| WO | WO 2012/141554 | 4/2012 |
| WO | WO 2013/065314 | 3/2013 |
| WO | WO 2014/018278 | 1/2014 |
| WO | WO 2014/039794 | 3/2014 |
| WO | WO 2014/043247 | 3/2014 |
| WO | WO 2014/125290 | 8/2014 |
| WO | WO 2014/162305 | 10/2014 |
| WO | WO 2015/155660 | 10/2015 |
| WO | WO 2016/075405 | 5/2016 |
| WO | WO 2016/118886 | 7/2016 |
| WO | WO 2016/196347 | 12/2016 |

OTHER PUBLICATIONS

Kim, "Overview of Cotinine Cutoff Values for Smoking Status Classification", 2016, International Journal of Environmental Research and Public Health, 13(12): 1236 (Year: 2016).*

Sajid, "Design, formats and applications of lateral flow assay: A literature review", 2014, Journal of Saudi Chemical Society, vol. 19, p. 689-705 (Year: 2014).*

Alwis et al., "Acrolein Exposure in U.S. Tobacco Smokers and Non-Tobacco Users: NHANES 2005-2006," Environ Health Perspectives, vol. 123, May 29, 2015, pp. 1302-1308.

Alwis et al., Simultaneous Analysis of 28 Urinary VOC Metabolites Using Ultra High Performance Liquid Chromatography Coupled with Electrospray Ionization Tandem Mass Spectrometry, Analytica Chimica ACTA, vol. 750, Apr. 12, 2012, pp. 152-160.

Arffin et al., "Environmental Tobacco Smoke and Stress of Risk Factors for Miscarriage and Preterm Births", Archives of Gynecology and Obstetrics | 286 (5): 1187-1191 Nov. 2012.

Auer et al., "Serum Cotinine Does Not Predict Neutralizing Antibodies Against Interferon Beta in an Austrian MS Cohort," Journal of Interferon and Cytokine Research | 36 (12): 667-670 Dec. 2016.

Babhadiashar et al., "Correlation Between Cigarette Smoking and Urine Cotinine Level in Gastric Cancer Patients", Iranian Journal of Pharmaceutical Research | 13 (1): 313-318 WIN 2014.

Bahadir et al., "Lateral Flow Assays: Principles, Designs and Labels," TrAC Trends in Analytical Chemistry, vol. 82, Sep. 2016, pp. 286-306.

Balhara, "A Comparative Study of Reliability of Self Report of Tobacco Use Among Patients with Bipolar Disorder and Somatoform Disorder", Biological Psychiatry | 71 (8): 169S-169S Suppl. S Apr. 15, 2012.

Biemann, "Sequencing of Peptides by Tandem Mass Spectrometry and High-Energy Collison-Induced Dissociation,", 1990. Methods Enzymol 193: 455-79.

Bono et al., "Oxidative Stress in Adolescent Passive Smokers Living in Urban and Rural Environments," Int J Hyg Environ Health, Mar. 2014;217(2-3):287-93.

Buacharoen et al., "The Urinary Cotinine and Serum 25 Hydroxyvitamin D Levels in Male Smokers," J Med Assoc Thai. Jun. 2012;95 Suppl 6:S87-93.

(56) References Cited

OTHER PUBLICATIONS

Carbone et al., "An Overview of the Latest Graphene-Based Sensors for Glucose Dectection: The Effects of Graphene Defects", Electroanalysis 2015, 27, 1-16.
Carlsten et al., "Cotinine Versus Questionnaire: Early Life Environmental Tobacco Smoke Exposure and Incident Asthma," BMC Pediatr, Dec. 5, 2012;12:187.
Chapman, "Mass Spectrometry of Proteins and Peptides", Methods in Molecular Biology, vol. 146: Humana Press 2000, ISBN 089603609x.
Chen et al., "Simultaneous, Rapid, and Sensitive Quantification of 8-Hydroxy-2'-Deoxyguanosine and Cotinine in Human Urine by On-Line Solid-Phase Extraction LC-MS/MS: Correlation with Tobacco Exposure Biomarkers NNAL", Analytical and Bioanalytical Chemistry, vol. 408, No. 23, Jul. 15, 2016.
Cheng et al., "Microfluidic Immunoassay for Rapid Detection of Cotinine in Saliva," Biomed Microdevices. Dec. 2013;15(6):949-57.
Clackson et al., "Making Antibody Fragments Using Phage Display Libraries," 1991 (Nature 352: 624-628).
Cocker et al., "Creatinine Adjustment of Biological Monitoring Results", Occupational Medicine (2011), vol. 61, issue 5, pp. 349-353.
Dinis-Oliveria, "Heterogeneous and Homogeneous Immunoassays for Drug Analysis", Bioanalysis (2014) 6(21), 2877-289.
Dixon et al., "Zinc Sulfate, a Recently Introduced Urinary Adulterant Can Invalidate urine Cotinine Test Using Immunoassay but has Less Effect on Liquid Chromatography Combined with Tandem Mass Spectrometry-Based Test," Ther Drug Monit. Oct. 2015;37(5):681-4.
Dixon, et al., Comparison of Semi-Quantitative Cotinine Values . . . , J Clin Lab Anal. Nov. 2016;30(6):1106-1109.
Durante et al., "Tobacco Smoke Exposure During Childhood . . . " Int J Environ Res Public Health, Oct. 24, 2013;10(11):5257-65.
Ebner et al., "Assessment of Serum Cotinine in Patients with Chronic Heart Failure: Self-Reported Versus Objective Smoking Behavior," Clin Res Cardiol. Feb. 2013;102(2):95-101.
El Sayed Desouky et al., "The Relation Between Exposure to Environmental Tobacco Smoke and the Quantity of Cotinine in the Urine of School Children in Taif City, Saudi Arabia," Asian Pac J Cancer Prev. 2016;17(l):139-45.
Ellington et al., "In Vitro Selection of RNA Modecules that Bind Specific Ligands", X1990 (Nature 346: 818-822).
Florescu et al., "Methods for Quantification of Exposure to Cigarette Smoking and Environmental Tobacco Smoke: Focus on Developmental Toxicology," Ther Drug Monit. Feb. 2009; 31(1): 14-30.
Frens, "Controlled Nucleation for the Regulation of the Particle Size in Monodisperse Gold Suspensions", 1973 Nature Physical Science, 241:20 (1973).
Garrabou et al., "Molecular Basis for Reduced Birth Weight in Smoking Pregnant Women: Mitochondrial Dysfunction and Apoptosis", Addiction Biology | 21 (1): 159-170 Jan. 2016.
Ghosh et al., "The Role of AHPCO Technology etc.," Journal of Allergy and Clinical Immunology | 135 (2): AB70-AB70 Suppl. S Feb. 2015.
Govind et al., "Pitfalls in the Assessment of Smoking Status Detected in a Cohort of South African RA Patients," Rheumatology International | 36 (10): 1365-1369 Oct. 2016.
Hamad et al., "Impact of Cigarette Smoking on Histone (H2B) to Protamine Ratio in Human Spermatozoa and its Relation to Sperm Parameters", ANDROLOGY 2 (5): 666-677 Sep. 2014.
Haziza et al. (2017) Data in Brief 10, 283-293.
Hoseini, "Biomonitoring of Tobacco Smoke Exposure and Self-Reported Smoking Status Among General Population of Tehran, Iran," Environ Sci Pollut Res Int. Dec. 2016;23(24):25065-25073.
Hou et al., "A col. Switching Liquid Chromatography-Tandem Mass Spectrometry Method . . . ", AnalBiochem. (2012) 430(1):75-82.
Jain et al., "Biochemical Validation of Self-Reported Smokeless Tobacco Abstinence Among Smokeless Tobacco Users: Results from a Clinical Trial of Varenicline in India," Journal of Psychoactive Drugs | 47 (4): 331-335 Aug. 8, 2015.

Jain et al., "Distributions of Selected Urinary Metabolites of Volatile Organic Compounds by Age, Gender, Race/Ethnicity, and Smoking Status in a Representative Sample of U.S. Adults," vol. 40, No. 2, Sep. 1, 2015, pp. 471-479.
Kavalkova et al., "The Incidence of Respiratory Symptoms and Their Associations with Serum Cotinine Levels as a Marker of Tobacco Smoking in 25-45 year old Novosibirsk Dwellers", Ter Arkh, 2016;88(1):70-4, Russian.
Kim et al., "Application of Bispecific Antibody Against Antigen and Hapten for Immunodetection and Immunopurification," Exp Mol Med. Sep. 27, 2013;45:e43.
Kim et al., "In Vitro and In Vivo Application of Anti-Cotinine Antibody and Cotinine-Conjugated Compounds", BMB Rep. Mar. 2014;47(3):130-4.
Ko et al., "Evaluation of Serum Cotinine Cut-Off to Distinguish Smokers from Nonsmokers in Korean Population", Ann Lab Med. Sep. 2016;36(5):427-33.
Kobayashi et al., "Combined Effects of AHR, CYP1 Al, and XRCC1 Genotypes and Prenatal Maternal Smoking on Infant Birth Size? Biomarker Assessment in the Hokkaido Study," Reproductive Toxicology | 65: 295-306 Oct. 2016.
Koczula et al., "Lateral Flow Assays," Essays Biochem. Jun. 30, 2016; 60(1): 111-120.
Kohler et al., "Continuous Cultures of Fused Cells Secreting Antibody of Predefined Specificity," 1975 (Nature 256: 495).
Kowalska et al., "The Influence of Biological and Environmental Factors on Metallothionein Concentration in the Blood," Journal of Trace Elements in Medicine and Biology | 29: 99-103 2015.
Kuhn et al., "Fast and Sample Cleanup-free Measurement of Nicotine and Cotinine by Stable Isotope Dilution Ultra-Performance Liquid Chromatography-Tandem Mass Spectrometry," J Pharm Biomed Anal. Aug.-Sep. 2012;67-68:137-43.
Lee et al., "The Accuracy of Urinary Cotinine Immunoassay Test Strip as an Add-n Test to Self-Reported Smoking Before Major Elective Surgery," Nicotine Tob Res.Oct. 2013;15(10):1690-5.
Lei et al., "Development and Comparison of Two Competitive ELISAs for Estimation of Cotinine in Human Exposed to Environmental Tobacco Smoke," Drug Test Anal. Oct. 2014;6(10):1020-7.
Leung et al., "Relationship Between Passive Smoking Exposure and Urinary Heavy Metals and Lung Functions in Preschool Children," Pediatr Pulmonol. Nov. 2013;48(11):1089-97.
Ling et al., "Multiplexing Molecular Diagnostics and Immunoassays Using Emerging Microarray Technologies," 2007. Expert Rev Mol Diagn 7: 87-98.
Lo, "Antibody Engineering: Methods and Protocols", Methods in Molecular Biology, vol. 248: Humana Press 2004, ISBN 1588290921.
Mak et al., "Trends in Analytical Chemistry", TrAC Trends in Analytical Chemistry, vol. 79, May 2016, pp. 297-305.
Marks et al., "By-Passing Immunization, Human Antibodies from V-gene Libraries Displayed on Phage," 1991 (J Mol Biol 222: 581-597).
Maska et al., "Serum Cotinine as a Biomarker of Tobacco Exposure and the Association with Treatment Response in Early Rheumatoid Arthritis," Arthritis Care & RESEARCH | 64 (12): 1804-1810 Dec. 2012.
Morales et al., "Accuracy of Self-Reported Tobacco Use in Newly Diagnosed Cancer Patients," Cancer Causes & Control | 24 (6): 1223-1230 Jun. 2013.
Mouhamed et al., "Risque d-Hyperthyroidie Dans Une Population de Fumerus Tunisiens," Annales De Biologte Clinique | 70 (2): 199-206 Mar.-Apr. 2012.
Nian et al., "Electrochemical Immunoassay of Cotinine in Serum Based on Nanoparticle Probe and Immunochromatographic Strip," Analytica Chhimica Acta | 713: 50-55 Feb. 3, 2012.
Nielsen et al., "Multiplexed Sandwich Assays in Microarray Format," 2004. J Immunol Methods 290: 107-20.
Niemela et al., "Prenatal Nicotine Exposure and Risk of Schizophrenia Among Offspring in a National Birth Cohort," Am J Psychiatry, Aug. 1, 2016;173(8):799-806.
Oyama et al., "One-Shot in Vitro Evolution Generated an Antibody Fragment for Testing Urinary Cotinine with More Than 40-fold Enhanced Affinity," Analytical Chemistry | 89 (1): 988-995 Jan. 3, 2017.

(56) References Cited

OTHER PUBLICATIONS

Park et al., "Cotinine-Conjugated Aptamer/Anti-Cotinine Antibody Complexes as a Novel Affinity Unit for Use in Biological Assays," Experimental and Molecular Medicine | 44 (9): 554-561 Sep. 30, 2012.

Patrick et al., "Spontaneous Reductions in Smoking During Double-Bliind Buprenorphine Detoxification," Addictive Behaviors | 39 (9): 1353-1356 Sep. 2014.

Pattanayak et al., "Reliability of Self-Reported Tobacco Use in Bipolar Disorder . . . ", International Journal of Psychiatry in Medicine | 43 (2): 153-163 2012.

Proceedings: ACCR 106$^{th}$ Annual Meeting, Cancer Research | 75: —Suppl. 15 Aug. 1, 2015.

Raja et al., Diagnostic Methods for Detection of Cotinine Level in Tobacco Users: A Review, *J Clin Diagn Res*. Mar. 2016; 10(3): ZE04-ZE06.

Roepstorff et al., "Proposal for a Common Nomenclature for Sequence Ions in Mass Spectra of Peptides," Biomed. Mass Spectrom. (1984) 11, 601).

Sachiyo et al., "Effect of Passive Smoking Using Maternal and Neonatal Salivary Cotinine Measurements", Nursing Research | 61 (2): 148-152 Mar.-Apr. 2012.

Sajid et al., "Designs, Formats and Applications of Lateral Flow Assay: A Literature Review," Journal of Saudi Chemical Society, vol. 19, Issue 6, Nov. 2015, pp. 689-705.

Salzer et al., "Smoking as a Risk Factor for Multiple Sclerosis", Mult Scler. Jul. 2013;19(8):1022-7.

Schettgen et al., "A Method for the Quantification of Biomarkers of Exposure to Acrylonitrile and 1,3-Butadiene in Human Urine . . . ", Anal. Bioanal. Chem. (2009) 393:969-981.

Schwarz et al., "Red Wine Prevents the Acute Negative Vascular Effects of Smoking", American Journal of Medicine | 130 (1): 95-100 Jan. 2017.

SER Abstracts, American Journal of Epidemiology | 177: S103-S103 Suppl. 11 Jun. 15, 2013.

Singh et al., "A Receiver Operated Curve-Based Evaluation of Change in Sensitivity and Specificity of Cotinine Urinalysis for Detecting Active Tobacco Use," Journal of Cancer Research and Therapeutics | 9 (1): 84-89 Jan.-Mar. 2013.

Sliwinska-Mosson et al., "The Effect of Smoking on Endothelin-1 in Patients with Chronic Pancreatitis", Applied Immunohistochemistry & Molecular Morphology | 23 (4): 288-296 Apr. 2015.

Surya et al., "Chairside Quantitative Immunochromatographic Evaluation of Salivary Cotinine and its Correlation with Chronic Periodontitis," J Indian Soc Periodontol. Oct. 2012;16(4):508-12.

Szumska et al., "Medicine Students and Exposure to Environmental Tobacco Smoke," International Journal of Occupational Medicine and Environmental Health | 26 (2): 313-320 2013.

Takeuchi et al., "Salivary Levels of Antibacterial Peptide (LL-37/hCAP-18) and Continine in Patients with Chronic Periodontitis," Journal of Periodontology | 83 (6): 766-772 Jun. 2012.

Tiede et al., "Affimer Proteins are Versatile and Renewable Affinity Reagents," eLife (2017) 6: e24903.

Toshihiro et al., "Urinary Biomarkers for Secondhand Smoke", Journal of Clinical Laboratory Analysis, vol. 25, No. 5, Jan. 1, 2011, pp. 354-358.

Tuerk et al., "Systematic Evolution of Ligands by Exponential Enrichment: RNA Ligands to Bacteriophage T3 DNA Polymerase," 1990 (Science 249: 505-510).X.

Vlasceanu et al., "Quntitative Relationships of Urinary Cotinine Levels in Smoking Diabetic Patients," FARMACIA | 63 (3): 349-356 May-Jun. 2015.

Wilson et al., "Secondhand Smoke Exposure and Serum Cytokine Levels in Healthy Children", CYTOKINE | 60 (1): 34-37 Oct. 2012.

Woeller et al., "Detection of Serum microRNAs from Department of Defense Serum Repository," J Occup Environ Med. Aug. 2016;58(8 Suppl 1):S62-71.

Wojas-Krawcyzk et al., "The Polymorphism of the CHRNA5 Gene and the Strength of Nicotine Addiction in Lung Cancer and COPD Patients," European Journal of Cancer Prevention | 21 (2): 111-117 Mar. 2012.

Xie et al., "Influence of CYP2A6*4 Genotypes of Maternal Serum Cotinine Among Chinese NonSmoking Pregnant Women," Nicotine Tob Res. Apr. 2014;16(4):406-12. doi: 10.1093/ntr/ntt164.

Yao et al., "Tobacco Smoke Exposure and Multiplexed Immunoglobulin E Sensitization in Children: A Population-Based Study," ALLERGY | 71 (1): 90-98 Jan. 2016.

Yoon et al., "Bispecific Her2 x Continine Antibody in Combination with Cotinine-(Histidine)2-Iodine for the Pre-Targeting of Her2-Positive Breast Cancer Zenografts," J Cancer Res Clin Oncol. Feb. 2014;140(2):227-33.

Japanese Office Action for Application No. 2019-554369 dated Mar. 16, 2022 (9 pages). English translation included.

Decision to Grant issued in Russia for Application No. 2019129545 dated May 4, 2022 (9 pages).

Montalto et al., "Validation of Self-Reported Smoking Status Using Saliva Cotinine: A Rapid Semiquantitative Dipstick Method", Cancer Epidemiol Biomarkers Prev 2007; 16(9), Sep. 2007.

Kalmykova et al., Razrabotrka Pjezokvartsevyh Immunisupressorov Dlya Protochno-Injektsionnogo Anayza Vysoko-I Nizko Molekulyarnyh Soeddynrniy//Vestnyk Moskovskogo Universiteya seriay 2. Chimiya, 2002, T. 43. N 6, p. 399-403. (in Russian only),.

* cited by examiner

DIAGNOSTIC TEST FOR DISTINGUISHING THE SMOKING STATUS OF A SUBJECT

This application is a U.S. National Stage Application of International Application No. PCT/EP2018/063228 filed May 18, 2018, which was published in English on Nov. 22, 2018, as International Publication No. WO 2018/211126 A1. International Application No. PCT/EP2018/063228 claims priority to European Application No. 17172100.4 filed May 19, 2017.

FIELD OF THE INVENTION

The present invention relates, in general, to the field of biological diagnostics. In particular, the invention relates to methods, devices, systems and kits to determine or distinguish the smoking status of a subject.

BACKGROUND

A number of aerosol generating articles in which tobacco is heated rather than combusted have been proposed in the art. In heated aerosol generating articles, an aerosol is generated by heating a substrate, such as tobacco. Numerous studies have shown that heating tobacco to temperatures below pyrolysis and combustion temperatures has the potential to reduce or eliminate some toxicants found in cigarette smoke. Heating instead of burning tobacco, typically at temperatures lower than 300° C. is sufficient to release nicotine, but not high enough to cause significant pyrolysis. At these temperatures, the aerosol composition becomes simpler than that found in cigarette smoke. Many harmful and potentially harmful constituents (HPHCs) in cigarette smoke are formed due to the combustion of tobacco. Thus, lowering the temperature and heating the tobacco instead of burning it can substantially reduce or eliminate HPHCs. Known heated aerosol generating articles include, for example, electrically heated aerosol generating articles and aerosol generating articles in which an aerosol is generated by the transfer of heat from a combustible fuel element or heat source to a physically separate aerosol forming material.

During smoking, volatile compounds are released from the aerosol forming substrate by heat transfer from the fuel element and entrained in air drawn through the aerosol generating article. As the released compounds cool they condense to form an aerosol that is inhaled by the consumer. Also known are aerosol generating articles in which a nicotine-containing aerosol is generated from a tobacco material, tobacco extract, or other nicotine source, without combustion, and in some cases without heating, for example through a chemical reaction.

These smoke-free alternatives (for example, heat not burn products) in which tobacco is heated rather than combusted offers smokers alternatives to conventional cigarettes, which may reduce harmful chemicals released from the tobacco while still delivering nicotine.

There is a need in the art for a rapid, cost effective, and easy to use diagnostic test to distinguish or determine the smoking status of a subject. For example, there is a need in the art to distinguish or determine current smokers of conventional cigarettes from those who have switched to a smoke-free alternative or who have abstained from smoking. Such a test will have a variety of applications. For example, the test could be used in clinical trials for identifying and screening of subjects based on their smoking status. By way of further example, the test could be used for insurance purposes as a compliance test to monitor switching to a smoke-free alternative and compliance with the switch. The present invention seeks to address these and other needs.

SUMMARY OF THE INVENTION

There is disclosed herein methods, devices, systems and kits in which at least two metabolites are detected to distinguish or determine the smoking status of a subject. The metabolites can be used as tobacco smoke exposure biomarkers. For example, a current smoker of conventional cigarettes can be distinguished from a subject who has switched to a smoke-free alternative (for example, a heat-not-burn product) or who has abstained from smoking. By way of further example, a smoker of a smoke-free alternative can be distinguished from a subject who has abstained from smoking. In addition to cotinine, which is no longer detectable in urine, saliva or blood after about two days of smoking abstinence, but which will still be present in switchers to a smoke-free alternative, one or two other tobacco smoke exposure biomarkers can be detected in urine. One such metabolite is 4-(methylnitrosamino)-1-(3-pyridyl)-1-butanol (NNAL), which is a metabolite of nicotine-derived nitrosamine ketone (NNK) (also known as 4-(methylnitrosamino)-1-(3-pyridyl)-1-butanone, a tobacco specific nitrosamine), usually measured in the urine with a half-life estimated at 17 hours. Another metabolite is 2-cyanoethylmercapturic acid (CEMA), which is a metabolite of acrylonitrile (a volatile compound from combustible tobacco products). In certain embodiments, only cotinine and total NNAL are measured. In other words, cotinine and total NNAL are exclusively measured as tobacco smoke exposure biomarkers. Total NNAL means NNAL and NNAL-Gluc. In certain embodiments, only cotinine and CEMA are measured. In other words, cotinine and CEMA are exclusively measured as tobacco smoke exposure biomarkers. In certain embodiments, only cotinine and total NNAL and CEMA are (exclusively) measured. In other words, total NNAL and CEMA are exclusively measured as tobacco smoke exposure biomarkers. Accordingly, the metabolites to be detected as tobacco smoke exposure biomarkers consist only of cotinine and total NNAL and/or CEMA.

In other words, the metabolites to be detected as tobacco smoke exposure biomarkers are exclusively cotinine and total NNAL and/or CEMA. These metabolites are indicative of the smoking status of an individual and disappear from urine with time upon switching to a smoke free product, while nicotine metabolites remain present. In one embodiment, the diagnostic test utilises urine—such as 24-hour urine. Suitably, the diagnostic test provides two or three readings for: cotinine; and total NNAL and/or CEMA. Suitably, the diagnostic test provides three or four readings: two or three readings for: cotinine; total NNAL and/or CEMA; and a positive control to demonstrate that the test works for subjects who do not have any tobacco metabolite in their urine. The positive control can be, for example, creatinine or albumin or a urine specific protein—such as Tamm-Horsfall protein (THP).

Other forms of control can be added or included—such as controls to measure the integrity, in particular, non-adulteration, of the sample to be tested as described herein.

In one aspect, there is described a device for determining the smoking status of a subject, wherein said device comprises a plurality of different specific binding molecules deposited onto a solid phase to detect the presence of two or three tobacco smoke exposure biomarkers in a biological sample, said tobacco smoke exposure biomarkers consisting of: (i) cotinine and total 4-(methylnitrosamino)-1-(3-pyridyl)-1-butanol (NNAL); or (ii) cotinine and N-acetyl-S-[2-carboxyethyl]-L-cysteine (CEMA); or (iii) cotinine and NNAL and CEMA.

Suitably, the device is a portable lateral flow immunoassay device, preferably, a dipstick, configured to perform a competitive immunoassay.

Suitably, the portable lateral flow immunoassay device comprises: (i) a sample pad; (ii) a conjugate pad; and (iii) at least one detection zone.

Suitably, the conjugate pad comprises or consists of labelled specific binding agents each capable of individually binding: (i) cotinine and NNAL; or (ii) cotinine and CEMA; or (iii) cotinine and NNAL and CEMA, suitably, wherein each of the labelled specific binding agents is an antibody or fragment thereof, an aptamer, a photoaptamer, an affimer, a protein, a peptide, a peptidomimetic or a small molecule.

Suitably, (a) the conjugate pad comprises or consists of labeled specific binding agents deposited thereon each capable of individually binding the metabolites: (i) cotinine and NNAL; or (ii) cotinine and CEMA; or (iii) cotinine and NNAL and CEMA, and capable of forming labeled specific binding agent metabolite conjugates; and (b) the detection zone comprises or consists of immobilised specific binding agents each capable of individually binding to the metabolites.

Suitably, (a) the conjugate pad comprises or consists of labelled metabolite(s) deposited thereon, said labelled metabolite(s) consisting of: (i) labelled cotinine or an analogue thereof and labelled NNAL or an analogue thereof; or (ii) labelled cotinine or an analogue thereof and labelled CEMA or an analogue thereof; or (iii) labelled cotinine or an analogue thereof and labelled NNAL or an analogue thereof and labelled CEMA or an analogue thereof; and (b) the detection zone comprises or consists of immobilised specific binding agents each capable of individually binding: (i) the labelled cotinine or the analogue thereof and the labelled NNAL or the analogue thereof and cotinine and NNAL that may present in a sample; or (ii) the labelled cotinine or the analogue thereof and the labelled CEMA or the analogue thereof and cotinine and CEMA that may be present in a sample; or (iii) the labelled cotinine or the analogue thereof and the labelled NNAL or the analogue thereof and the labelled CEMA or the analogue thereof and cotinine and NNAL and CEMA that may be present in a sample.

Suitably, the specific binding molecules are labelled with colored particles, suitably, gold nanoparticles and optionally, and wherein the labels for each of the specific binding molecules are the same or different.

Suitably, the threshold is: (i) greater than or equal to about 200 ng/ml for 24 hour urinary cotinine and greater than or equal to about 10 pg/ml for total NNAL in 24 hour urine or greater than or equal to about 5 ng/ml for 24 hour urinary CEMA; or (ii) greater than or equal to about 200 ng/ml for 24 hour urinary cotinine and greater than or equal to about 10 pg/ml for total NNAL in 24 hour urine and greater than or equal to about 5 ng/ml for 24 hour urinary CEMA.

Suitably, the device is adapted to detect: (i) 24 hour urinary cotinine in an amount of between about 200-800 ng/ml; or (ii) 24 hour urinary total NNAL in 24 hour-urine in an amount of between about 10-125 pg/ml; or (iii) 24 hour urinary CEMA in an amount of between about 5-80 ng/ml; or (iv) a combination of at least two of (i), (ii), and (iii).

Suitably, (i) visible indication of (i) cotinine and NNAL; or (ii) cotinine and CEMA; or (iii) cotinine and NNAL and CEMA on a test line(s) of the device indicates that the threshold of detection has not been crossed and is indicative of a non-smoking subject; (ii) no visible indication of (i) cotinine and NNAL; or (ii) cotinine and CEMA; or (iii) cotinine and NNAL and CEMA on a test line of the device indicates that the threshold of detection has been crossed and visible indication of (i) cotinine and NNAL; or (ii) cotinine and CEMA; or (iii) cotinine and NNAL and CEMA on a test line of the device indicates that the threshold of detection has not been crossed and is indicative of a subject exposed to heated tobacco; (iii) no visible indication of (i) cotinine and NNAL; or (ii) cotinine and CEMA; or (iii) cotinine and NNAL and CEMA on a test line of the device indicates that the threshold of detection has been crossed and is indicative of a subject exposed to combusted tobacco.

In another aspect, there is disclosed a device for determining the smoking status of a subject comprising: (a) a receptacle adapted for receiving the device described herein; (b) an imaging device adapted to acquire at least one digital image of the device; and (c) a processor adapted to process the at least one digital image.

In another aspect, there is disclosed a system comprising: (a) a computer data repository that comprises or consists of a reference or baseline value of the quantity of cotinine and one or more of total NNAL and CEMA, said reference or baseline values representing a known quantity of metabolite for determining the smoking status of a subject; and (b) a computer system programmed to access the data repository and to use information from the data repository in combination with information on the quantity of metabolites in the sample from a subject, to make a determination of the smoking status of the subject.

In another aspect, there is disclosed a kit comprising the device described herein and optionally, a set of instructions for operating the kit and optionally a set of instructions for determining the smoking status of a subject.

In another aspect, there is disclosed a method for determining the smoking status of a subject comprising the use of the device described herein.

In another aspect, there is disclosed a method for determining the smoking status of a subject, said method comprising: (a) detecting the amounts of (i) cotinine and NNAL; or (ii) cotinine and CEMA; or (iii) cotinine and NNAL and CEMA in a sample, wherein said metabolites consist of cotinine and NNAL and CEMA, comprising contacting the sample with anti-cotinine and anti-NNAL and anti-CEMA specific binding agent and detecting binding; and (b) determining the smoking status of the subject; wherein if the amount of cotinine is between about 10.6 and 41.5 ng/ml in 24 hour urine at day 5 of an investigational period is indicative of a smoking abstainer; and if the amount of total NNAL is between about 37.7 pg/ml and 115 pg/ml in 24 hour urine and the amount of CEMA is about 31.1 ng/ml and 90 ng/ml in 24 hour urine at day 5 of an investigational period is indicative of a subject exposed to combusted tobacco; and if the amount of cotinine is between about 652.5 and 1115 ng/ml ng/ml or more in 24 hour urine at day 5 of an investigational period is indicative of a subject exposed to heated tobacco.

There is also disclosed a method of monitoring the progression of a subject's change in smoking status comprising: (i) performing the method described herein on at least two biological samples from the subject, wherein each sample is taken at different time points; and (ii) comparing the measurements taken for each of the different time points, wherein a change in the measurements over time is indicative that the subject's smoking status has changed over time.

A method for determining the smoking status of a subject is also disclosed comprising: (i) receiving data representative of values of the quantity of two or three metabolites in a sample from a subject, said metabolites consisting of cotinine and one or more of total NNAL and CEMA; (ii) accessing a data repository on a computer, said data repository comprising a reference or baseline value for the quantities of cotinine and total NNAL and/or CEMA that are diagnostic for determining the smoking status of a subject; and (iii) comparing the data as received in (i) with the reference or baseline value in the data repository on the computer recited in (ii), thereby determining the smoking status in the subject.

There is also disclosed a method of distinguishing or determining the smoking status of a subject, said method comprising: (i) obtaining or providing a sample from a subject; (ii) detecting the amounts of two or three metabolites in the sample, wherein said metabolites consist of cotinine and total NNAL and/or CEMA, by contacting the sample with anti-cotinine and anti-total NNAL and/or anti-CEMA antibody or fragment thereof and detecting binding between cotinine and total NNAL and/or CEMA and the antibodies; and (iii) determining the smoking status of the subject based on detecting the presence of cotinine and total NNAL and/or CEMA in the sample.

A further aspect relates to a method of determining the smoking status of a subject and administering one or more therapies to reduce smoking of conventional cigarettes, said method comprising: (i) obtaining or providing a sample from a subject; (ii) detecting whether two or three metabolites are present in the sample, said metabolites consisting of cotinine and total NNAL and/or CEMA; (iii) determining the smoking status of the subject; and (iv) depending on the result obtained in (iii) administering an effective amount of one or more therapies to reduce smoking of conventional cigarettes.

A further aspect relates to a method of diagnosing and reducing the smoking of conventional cigarettes in a subject, said method comprising: (i) obtaining a sample from a subject; (ii) detecting whether cotinine and one or more of total NNAL and CEMA is present in the sample; and (iii) in a subject diagnosed as a smoker, administering an effective amount of one or more therapies to reduce the smoking of conventional cigarettes in the subject.

The present methods may be adequately qualified as in vitro or ex vivo uses, in that they apply particular in vitro or ex vivo processing and analysis steps on a sample obtained from a subject.

The method may be performed on a subject at two or more successive time points and the respective outcomes at said successive time points may be compared, whereby the presence or absence of a change between the detection of cotinine, total NNAL and/or CEMA at said successive time points is determined. When so applied, the method may be used to monitor a change in the detection of cotinine, total NNAL and/or CEMA in the subject over time. For example, a deviation of the quantity of the metabolite(s) in a sample from a subject compared to a baseline or reference value may be indicative of the smoking status of a subject.

In certain embodiments, the determination of what action is to be taken, e.g., by a clinician or company, in view of said detection is performed by a computer. In certain embodiments, a computer can be used to report the results and/or action to be taken.

In certain embodiments, an algorithm may be developed, based on the sum of the individual scores between 0 and 1 attributed to each specific metabolite level measured in the sample of the subject. Smoking status may then be predicted if said sum crosses a certain threshold. In some embodiments, the weight of each individual metabolite score may be adjusted to improve the performance of the algorithm.

There is also provided a kit for determining the smoking status of a subject comprising or consisting of: (i) a first device adapted to detect the presence of a tobacco smoke exposure biomarker in a biological sample, wherein said tobacco smoke exposure biomarker consists of cotinine; (ii) a second device adapted to detect the presence of a tobacco smoke exposure biomarker in a biological sample, wherein said tobacco smoke exposure biomarker consists of NNAL; and/or (iii) a third device adapted to detect the presence of a tobacco smoke exposure biomarker in a biological sample, wherein said tobacco smoke exposure biomarker consists of CEMA; and optionally, a set of instructions for operating the kit and optionally a set of instructions for determining the smoking status of a subject.

Some Advantages

The present disclosure provides a rapid, cost effective, and easy to use diagnostic test to determine, decipher or distinguish the smoking status of a subject. The present disclosure may have improved discriminatory power as compared to other tests to determine the smoking status of a subject.

The present disclosure may have improved discriminatory power to determine the smoking status of certain kinds of subjects in the population. For example, the discriminatory power may be greater in certain ethnical groups or in certain age populations.

Advantageously, the present disclosure can allow for the simultaneous detection of urinary total NNAL, urinary CEMA and urinary cotinine. In particular, the present disclosure can allow for the simultaneous detection of urinary total NNAL in 24 hour-urine in an amount of about 10-125 pg/ml and urinary CEMA in 24 hour urine in an amount of about 5-80 ng/ml and urinary cotinine in an amount of about 200-800 ng/ml to determine or distinguish the smoking status of a subject. The present disclosure may have improved discriminatory power to determine the smoking status of a subject who uses mentholated and non-mentholated smoking products. Menthol cigarettes are generally constructed in a similar way to non-mentholated cigarettes, with menthol added at any one of several stages during the manufacturing process. Menthol may be derived from, for example, distilled corn mint oil or produced synthetically. A menthol cigarette typically has at least 0.3% menthol content by weight Lower-tar menthol cigarettes may have menthol levels of up to 2%. Compared to tobacco blends for non-mentholated cigarettes, a menthol cigarette will tend to have more flue-cured than burley tobacco, and less oriental tobacco.

DEFINITIONS

Figure 1:
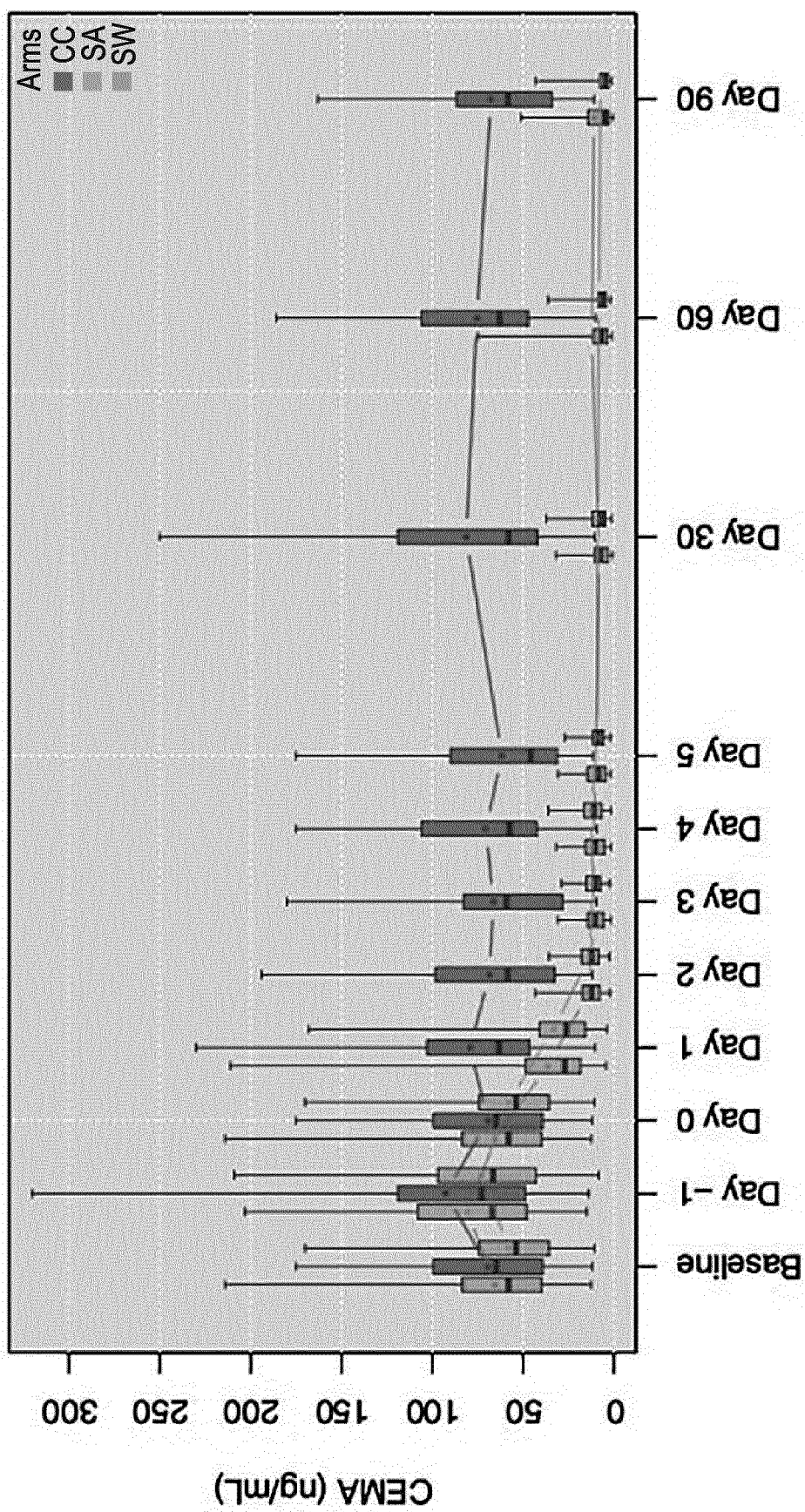
FIG. 1: CEMA: The bottom of the box is the first quartile (value below which 25% of the observations lie), the top is the third quartile (value below which 75% of the observations lie) and the middle bar is the median of the observations. The whiskers extend to the minimum observed value and maximum observed value respectively.

Section headings as used in this disclosure are for organisation purposes and are not intended to be limiting. Unless otherwise defined, all technical and scientific terms used herein have the same meaning as commonly understood by one of ordinary skill in the art.

In case of conflict, the present document, including definitions, will control. Preferred methods and materials are described below, although methods and materials similar or equivalent to those described herein can be used in practice or testing of the present invention. The materials, methods, and examples disclosed herein are illustrative only and not intended to be limiting. As used herein, the singular forms "a", "an", and "the" include both singular and plural referents unless the context clearly dictates otherwise.

The term "and/or" means (a) or (b) or both (a) and (b).

The terms "comprising", "comprises" and "comprised of" as used herein are synonymous with "including", "includes" or "containing", "contains", and are inclusive or open-ended and do not exclude additional, non-recited members, elements or method steps. The term "consisting of" means that additional components are excluded and has the recited elements only and no more.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosure. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

The term "smoker" is indicative of a subject that has smoked tobacco products in the past 5 years. The smoker will generally be a current smoker. Suitably, the smoker has smoked at least 100 tobacco products in his/her lifetime and may currently smoke tobacco every day or on some days (non-daily).

The term "non-smoker" as used herein means a subject that has previously been a smoker but has not smoked tobacco products in the past 5 years. The non-smoker will be deemed to have abstained from smoking.

The term "metabolite" is widespread in the art and may broadly denote any substance produced by metabolism or by a metabolic process. Expressed in another way, a metabolite is an end product resulting from metabolism. The term also encompasses a detectable portion of a metabolite whose qualitative and/or quantitative evaluation in a subject is, alone or combined with other data, informative with respect to the status of the subject as to switching compliance. The metabolites are typically small molecules derived from combustible tobacco products. Monitoring of the metabolites may inter alia over time may enable the progress of a subject's switching compliance to be determined over time.

The term "subject" as used herein typically denotes humans, but may also encompass reference to non-human animals, preferably warm-blooded animals, more preferably viviparous animals, even more preferably mammals, such as, e.g., non-human primates, rodents, canines, felines, equines, ovines, porcines, and the like.

The terms "sample" or "biological sample" as used herein include any biological specimen obtained from a subject. Samples may include, without limitation, whole blood, plasma, serum, red blood cells, white blood cells (e.g., peripheral blood mononuclear cells), saliva, urine, stool (i.e., faeces), tears, sweat, sebum, nipple aspirate, ductal lavage, tumour exudates, synovial fluid, cerebrospinal fluid, lymph, fine needle aspirate, amniotic fluid, any other bodily fluid, nail clippings, cell lysates, cellular secretion products, inflammation fluid, vaginal secretions, or biopsies such as preferably placental biopsies. Preferred samples may include those comprising any one or more metabolites as taught herein in detectable quantities. In one embodiment, the sample may be whole blood or a fractional component thereof such as, e.g., plasma, serum, or a cell pellet. Preferably the sample is readily obtainable by minimally invasive methods, allowing to detect, remove or isolate said sample from the subject. Samples may also include tissue samples and biopsies, tissue homogenates and the like. The term "plasma" generally denotes the substantially colourless watery fluid of the blood that contains no cells, but in which the blood cells (erythrocytes, leukocytes, thrombocytes, etc.) are normally suspended, containing nutrients, sugars, proteins, minerals, enzymes, etc. In a most suitable embodiment, the sample is urine—such as 24-hour urine as it is easy and non-invasive to obtain. A 24-hour urine collection is done by collecting a subject's urine in a container over a full 24-hour period.

A molecule, such as a metabolite, is "measured" in a sample when the presence or absence and/or quantity of said molecule or of said group of molecules is detected or determined in the sample, preferably substantially to the exclusion of other molecules. For example, a metabolite may be measured by laboratory tests as described herein.

The terms "quantity", "amount" and "level" are synonymous and generally well-understood in the art. With respect to metabolites, molecules or analytes, the terms may particularly refer to an absolute quantification of the metabolite, molecule or analyte in a sample, or to a relative quantification of the metabolite, molecule or analyte in the sample, i.e., relative to another value such as relative to a baseline or reference value as taught herein, or to a range of values indicating a base-line expression of the metabolite, molecule or analyte.

These values or ranges may be obtained from a single subject or from a group of subjects.

An absolute quantity of a metabolite, molecule or analyte in a sample may be advantageously expressed as weight or as molar amount, or more commonly as a concentration, e.g. weight per volume or mol per volume.

The term "threshold" in the context of detection means the point at which a certain or defined amount or quantity or concentration is reached or crossed. For example, a test line on an immunoassay device can be configured to produce a visual change when a threshold amount or quantity or concentration is reached or crossed.

The term "small molecule" refers to compounds, preferably organic compounds, with a size comparable to those organic molecules generally used in pharmaceuticals. The term excludes biological macromolecules (e.g., proteins, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

The term "isolated" as used herein may preferably also encompass the qualifier "purified". As used herein, the term "purified" with reference to a metabolite does not require absolute purity. Instead, it denotes that such metabolite(s) is (are) in a discrete environment in which their abundance (conveniently expressed in terms of mass or weight or concentration) relative to other molecules is greater than in a biological sample. A discrete environment denotes a single medium, such as for example a single solution, gel, precipitate, lyophilisate, etc. Purified metabolites may be obtained by known methods including, for example, chromatography, preparative electrophoresis, centrifugation, precipitation, affinity purification, etc.

The term "specifically bind" as used throughout this specification means that an agent (denoted herein also as "specific-binding agent") binds to one or more desired molecules substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold or more greater than its affinity for a non-target molecule. An example of a specific binding agent is an antibody or a fragment thereof, aptamer, affimer, photoaptamer, protein, peptide, peptidomimetic or a small molecule. Preferred specific binding agents are antibodies or fragments thereof, aptamers or affimers.

As used herein, the term "antibody" is used in its broadest sense and generally refers to any immunologic binding agent. The term encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

The term "aptamer" refers to single-stranded or double-stranded oligo-DNA, oligo-RNA or oligo-DNA/RNA or any analogue thereof, that may specifically bind to a target molecule such as a peptide. Advantageously, aptamers may display fairly high specificity and affinity (e.g., $K_A$ in the order $1 \times 10^9$ M$^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592. The term "photoaptamer" refers to an aptamer that contains one or more photoreactive functional groups that may covalently bind to or crosslink with a target molecule.

Concerning "investigational period", baseline measurements are taken by allowing a subject to smoke their chosen brand of conventional cigarette for 2 days. After this 2 day period, the subject then elects to continue smoking conventional cigarettes, to switch to a smoke-free alternative or to abstain from smoking. The investigational period then begins. The term "affimer" refers to a highly stable protein that binds its target molecule with similar specificity and affinity to that of antibodies. They are engineered non-antibody binding proteins designed to mimic the recognition capabilities of monoclonal antibodies. For example, these engineered proteins can be about 12-14 kDa and based on a consensus sequence of cystatin A from plant (Avacta, Cambridge, United Kingdom). See, for example, Tiede et al., eLife (2017) 6: e24903; WO2006/131749, WO2009/136182 and WO2014/125290.

DETAILED DESCRIPTION

Section headings as used in this disclosure are for organisation purposes and are not intended to be limiting.

Metabolites

The respective quantities or measurements for the metabolites used as tobacco smoke exposure biomarkers as described herein may be evaluated simultaneously, separately or individually. Suitably, the metabolites described herein are evaluated substantially simultaneously or simultaneously. Suitably, the metabolites described herein are evaluated simultaneously at the same point in time. The amounts of the metabolite(s) can be used to establish if a subject is a current smoker of conventional cigarettes. The amounts of the metabolite(s) can be used to establish if a subject is a consumer of a smoke-free alternative.

The amounts of the metabolite(s) can be used to establish if a subject has abstained from smoking. Conveniently, this can be carried out in a single test. In a particular embodiment, the amounts of the metabolites can advantageously be used to establish a switching profile for a subject to distinguish current smokers of conventional cigarettes from those who have switched to a smoke-free alternative or who have abstained from smoking. The switching compliance behaviour may be assessed over time to monitor the progression of the switching behaviour.

The metabolites can comprise or consist or consist essentially of cotinine and total NNAL, or cotinine and CEMA, or cotinine and total NNAL and CEMA. Suitably, the metabolites can be exclusively cotinine and total NNAL, or exclusively cotinine and CEMA, or exclusively cotinine and total NNAL and CEMA. Accordingly, the metabolites consist of cotinine and total NNAL, or consist of cotinine and CEMA, or consist of cotinine and total NNAL and CEMA. In certain embodiments it is intended to encompass isomeric forms (such as stereoisomers and/or geometric and/or optical isomers, and mixtures thereof), chemical derivatives, mimetics, variants, solvates and salts of these metabolites.

In addition to detecting the metabolites that are used as tobacco smoke exposure biomarkers, more general characteristics of a sample can be evaluated simultaneously, separately and/or individually. For example, to test for the adulteration or dilution of a sample, certain characteristics can be detected. For example, in the case of a urine sample, characteristics—such as one or more of pH, specific gravity, oxidants, nitrite, glutaraldehyde and creatinine levels—may be measured in the urine sample. These more general characteristics can be detected using the device for determining the smoking status of a subject, for example, by incorporating a further lateral flow test strip or the like into the device.

Cotinine

Nicotine is a tertiary amine which is composed of a pyridine and a pyrrolidine ring. It undergoes a large first pass effect during which the liver metabolizes 80-90% of the inhaled amount. The major metabolite of nicotine is cotinine; while nicotine-1'-N-oxide is a minor metabolite (only 4-7% of the nicotine absorbed by smokers). The transformation of nicotine into cotinine involves two steps: 1) CYP2A6 activation, and 2) oxidation by a cytoplasmic aldehyde oxidase. Cotinine is also extensively metabolized to trans-3'-hydroxycotinine. The most abundant metabolite in mice is trans-3'-hydroxycotinine, accounting for 40-60%, whereas cotinine itself accounts for only about 15% of the dose of nicotine. It is also the main nicotine metabolite detected in the urine of smokers. Cotinine levels in various biological fluids are widely used to estimate intake of nicotine in tobacco users. The usefulness of cotinine as a quantitative marker of nicotine intake is limited by individual variability in percentage conversion of nicotine to cotinine and in the rate of elimination of cotinine.

The total clearance rate of nicotine is about 1200 mL min-1. The metabolism of cotinine is much slower, with a total clearance averaging 45 mL min-1. Trans-3'-hydroxycotinine total clearance is also rather slow, about 82 mL min-1. Intravenous infusion of nicotine in abstinent adult smokers has shown half-lives of 2.3 h for nicotine, 17.5 h for cotinine and 6.6 h for trans-3'-hydroxycotinine.

Cotinine has an in vivo half-life of about 20 hours, and can be detected for several days after the use of tobacco use. The level of cotinine in blood, saliva, and urine is proportionate to the amount of exposure to tobacco smoke. Cotinine levels of <10 ng/mL are indicative with no active smoking. Values of 10 ng/mL to 100 ng/mL are indicative of light smoking or moderate exposure. Levels above 300 ng/mL are indicative of heavy smoker status consuming more than 20 cigarettes a day. In urine, values between 11 ng/mL and 30 ng/mL are indicative of light or moderate smoking, and levels in active smokers are about 500 ng/mL or more. In saliva, values between 1 ng/mL and 30 ng/mL are indicative of light or moderate smoking and levels in active smokers are about 100 ng/mL or more. Methods for detecting cotinine include colorimetric methods, gas chromatography (GC) and gas chromatography-mass spectrometry (GC-MS), high-performance liquid chromatography, and radioimmunoassay (RIA). Cotinine equivalent measurements may use cyanide and a chromophore-generating reagent for determination of pyridine derivatives (specifically nicotine metabolites). Other methods for detecting cotinine include the use of anti-cotinine antibody or a fragment thereof which can be converted into various formats, including a bispecific antibody. The anti-cotinine antibody or a fragment thereof can be applied to various formats—including immunoblot, enzyme immunoassay, immunoaffinity purification, and in vivo radioimmunoimaging and the like, as described herein. Methods for measuring cotinine are well documented in the art in, for example, in BMB Rep. (2014) March; 47(3): 130-134; *J Clin Diagn Res.* (2016) March; 10(3): ZE04-ZE06 and *Ther Drug Monit.* (2009) February; 31(1): 14-30.

Suitably, the devices and methods according to the present disclosure are configured to detect cotinine in urine in the range of from about 11 ng/ml to about 500 ng/ml, suitably in 24 hr urine after 5 days Suitably, the devices, methods and kits according to the present disclosure are configured to detect (free) cotinine in the range of between about 459 ng/ml to about 1350 ng/ml or between about 339-959 ng/ml or between about 546-1160 ng/ml. Suitably, these values are determined in urine, suitably 24 hr urine. Suitably, the devices, methods and kits according to the present disclosure are configured to detect (free) cotinine in the range of between about 200 ng/ml to about 800 ng/ml. Suitably, these values are determined in urine, suitably 24 hr urine.

Suitably, the devices, methods and kits according to the present disclosure are configured to detect (free) cotinine in the range of between about 11 ng/ml to about 30 ng/ml. Suitably, these values are determined in urine, suitably 24 hr urine.

Suitably, the devices, methods and kits according to the present disclosure are configured to visually display a result. The result can be determined using a machine or by eye. In certain embodiments, the result is determined by eye. In one embodiment, the devices, methods and kits are configured to visually display a result when a threshold level of cotinine that is greater than or equal to 200 ng/ml in 24 hour urine is crossed. In another embodiment, the devices, methods and kits and configured to visually display a result when a threshold level of cotinine that is greater than or equal to 300 ng/ml or 400 ng/ml or 500 ng/ml or 600 ng/ml in 24 hour urine in crossed.

NNAL

NNAL is a metabolite of 4-(methylnitrosamino)-1-(3-pyridyl)-1-butanone (NNK). Baseline levels of excreted total NNAL (NNAL and NNAL-Gluc) in the 24 h urine of smokers, are typically in the range of 1.1-2.9 nmol/24 h (i.e 230-607 ng/24 h). Neither NNAL nor NNN are in principle detectable in the urine of non-smokers, unless they use other tobacco products, nicotine replacement products, or are exposed to second-hand smoke, in which case levels are in the range of 0.1 nmol.

In a study, smokers consuming 20 CPD or more were required to smoke exactly 20, 15, 5 or 0 CPD during a 5-day confinement period. The results showed a dose-relationship between the number of cigarettes and the levels of urinary NNAL (i.e. 624, 549, 422 and 311 ng/24 h, respectively).

Because of the long half-life of NNAL, estimated to be between 10 and up to 45 days, NNAL levels in smoking cessation/abstinence studies of short duration do not reach the levels of non-smokers, and decrease by around 3- to 4-fold in studies lasting between 3 to 8 days. In a smoking cessation study lasting up to 56 days, levels of total NNAL reached levels described for non-smokers at the end of the study (i.e. 0.13 nmol/24 h at day 56 vs 2.70 nmol/24 h at baseline), and seemed to remain above these levels after 28 and 42 days (i.e. 0.26 and 0.2 nmol/24 h, respectively).

NNAL can be detected using any conventional methods that are known in the art including LC-MS/MS or GC/MS and the like. In addition, NNAL can be detected using an antibody or a fragment thereof which specifically binds to NNAL, optionally bound to an immunogenic carrier. Such antibodies are described in WO02009/010296.

Haziza et al. (2017) *Data in Brief* 10, 283-293 describes the levels of total NNAL in 24-hour urine. Baseline measurements are taken by allowing the subject to smoke their chosen brand of conventional cigarette for 2 days. After this 2 day period, the subject is then elected (i) to continue smoking conventional cigarettes, (ii) to switch to a smoke-free alternative or (iii) to abstain from smoking. After 5 days of the investigational period, 24-hour urine is then collected to measure the level of metabolite therein. In consumers of conventional cigarettes, baseline total NNAL is between 84-131 pg/mg creatinine (105 pg/mg creatinine). At day 5, this increases to between 85-133 pg/mg creatinine (107 pg/mg creatinine). Compared to baseline, this represents a −2.8% to 10.5% change (3.9% average increase).

In consumers of smoke-free alternatives, baseline total NNAL is between 95-129 pg/mg creatinine (111 pg/mg creatinine). At day 5, this decreases to between 42-58 pg/mg creatinine (49 pg/mg creatinine). Compared to baseline, this represents a −57% to −51% change (−54% average decrease).

In smoking abstainers, baseline total NNAL is between 94-150 pg/mg creatinine (119 pg/mg creatinine). At day 5, this decreases to between 31-54 pg/mg creatinine (41 pg/mg creatinine). Compared to baseline, this represents a −67 to −61% decrease (−63.9% average decrease).

Suitably, the devices, methods and kits according to the present disclosure are configured to detect total NNAL in the range of from about 10 pg/ml to about 125 pg/ml.

Suitably, the devices, methods and kits according to the present disclosure are configured to detect total NNAL in the range of from about 30 pg/mg creatinine to about 160 pg/mg creatinine.

Suitably, the devices, methods and kits according to the present disclosure are configured to detect total NNAL in the range of from about 85-133 pg/mg creatinine or about 85-125 pg/mg creatinine. Suitably, the devices, methods and kits according to the present disclosure are configured to detect total NNAL in the amount of about 107 pg/mg creatinine. These amounts are diagnostic for users of conventional cigarettes.

Suitably, the devices, methods and kits according to the present disclosure are configured to detect total NNAL in the range of from about 42-58 pg/mg creatinine. Suitably, the devices, methods and kits according to the present disclosure are configured to detect total NNAL in the amount of 49 pg/mg creatinine. These amounts are diagnostic for users of smoke-free alternatives.

Suitably, the devices, methods and kits according to the present disclosure are configured to detect total NNAL in the range of from about 31-54 pg/mg creatinine. Suitably, the devices, methods and kits according to the present disclosure are configured to detect total NNAL in the amount of 41 pg/mg creatinine. These amounts are diagnostic for abstainers of smoking.

Suitably, the devices, methods and kits according to the present disclosure are configured to detect total NNAL in the range of from about 33 ng/ml to about 132 pg/ml or from about 33 ng/ml to about 125 pg/ml or between about 2.5 and 46 pg/ml or between about 10 and 46 pg/ml or between about 37 and 115 ng/ml or between about 17-41 ng/ml. Suitably, these values are determined in urine, suitably 24 hr urine. Suitably, the devices, methods and kits according to the present disclosure are configured to visually display a result. The result can be determined using a machine or by eye. In certain embodiments, the result is determined by eye.

In certain embodiments, the result is determined by eye. In one embodiment, the devices, methods and kits and configured to visually display a result when a threshold level of NNAL that is greater than or equal to 10 pg/ml in 24 hour urine is crossed. In another embodiment, the devices, methods and kits and configured to visually display a result when a threshold level of NNAL that is greater than or equal to 10 pg/ml or 20 pg/ml or 30 pg/ml or 40 pg/ml in 24 hour urine is crossed.

CEMA

CEMA is a specific urinary biomarker of acrolein exposure. The main pathway by which acrolein is eliminated from the human body is through conjugation with glutathione (GSH) in the liver followed by enzymatic cleavage and N-acetylation to form S-(3-oxopropyl)-N-acetyl cysteine (OPMA) in the kidney. Reduction of the aldehyde group of OPMA forms 3HPMA, the major urinary metabolite of acrolein exposure, and oxidation of the aldehyde group of OPMA forms N-acetyl-S-[2-carboxyethyl]-L-cysteine (CEMA) as a minor metabolite.

Urinary excretion of CEMA has been shown to be consistently higher in smokers than in non-smokers. Ranges in non-smokers are usually below 2 ng/mL and increase to levels of more than 20 to 205 ng/mL in smokers. In a study, smokers excreted 187±181 µg/L (mean±SD) or 184 µg/L of CEMA, while non-smokers only excreted 4.6±35 µg/L or 1.9 µg/L.

Smokers consuming 20 CPD or more who were required to smoke exactly 20, 15, 5 or 0 CPD during a 5-day confinement period showed a dose-relationship between the number of cigarettes and the levels of urinary CEMA (i.e. 218.0, 168.0, 93.2 and 38.3 µg/24 h, respectively). Smoking cessation studies of 5 to 8 days showed significantly lower levels of CEMA in urine by about 7- to 10-fold.

Various methods are known in the art for measuring CEMA—such as ultra-high-performance liquid chromatography coupled with electrospray ionization tandem mass spectrometry. The determination of CEMA in urine has also been described in *Anal. Bioanal. Chem.* (2009) 393:969-981 and *Anal Biochem.* (2012) 430(1):75-82. In addition, CEMA can be detected using an antibody—such as a monoclonal antibody—or a fragment thereof, which specifically binds to CEMA, optionally bound to an immunogenic carrier. For example, the methods described in WO02009/010296 can be employed.

Haziza et al. (2017) *Data in Brief* 10, 283-293 describes the levels of CEMA in 24-hour urine. Baseline measurements are taken by allowing the subject to smoke their chosen brand of conventional cigarette for 2 days. After this 2 day period, the subject is then elected to continue smoking conventional cigarettes, to switch to a smoke-free alternative or to abstain from smoking. After 5 days of the investigational period, 24-hour urine is then collected to measure the level of metabolite therein.

In consumers of conventional cigarettes, baseline CEMA is between 83-115 ng/mg creatinine (98 ng/mg creatinine). At day 5, this increases to between 85-115 ng/mg creatinine (99.5 ng/mg creatinine). Compared to baseline, this represents a −4% to 12% change (4.2% average increase).

In consumers of smoke-free alternatives, baseline CEMA is between 85-112 ng/mg creatinine (98 ng/mg creatinine). At day 5, this decreases to between 11-15 ng/mg creatinine (13 ng/mg creatinine). Compared to baseline, this represents a −87% to −85% change (−86% average decrease).

In smoking abstainers, baseline CEMA is between 89-119 ng/mg creatinine (103 ng/mg creatinine). At day 5, this decreases to between 10-15 ng/mg creatinine (12 ng/mg creatinine). Compared to baseline, this represents a −88 to −85% decrease (−86% average decrease).

Suitably, the devices and methods according to the present disclosure are configured to detect CEMA in the range of from about 11 ng/mg creatinine to about 120 ng/mg creatinine.

Suitably, the devices and methods according to the present disclosure are configured to detect CEMA in the range of from about 11 ng/mg creatinine to about 80 ng/mg creatinine.

Suitably, the devices and methods according to the present disclosure are configured to detect CEMA in the range of from about 5 ng/mg creatinine to about 80 ng/mg creatinine.

These amounts are diagnostic for users of conventional cigarettes and readings are taken in 24 hour urine after 5 days of the investigational period.

Suitably, the devices, methods and kits according to the present disclosure are configured to detect CEMA in the range of from about 11-15 pg/mg creatinine. Suitably, the devices, methods and kits according to the present disclosure are configured to detect CEMA in the amount of 13 ng/mg creatinine. These amounts are diagnostic for users of smoke-free alternatives and readings are taken in 24 hour urine after 5 days of the investigational period.

Suitably, the devices, methods and kits according to the present disclosure are configured to detect CEMA in the range of from about 10-15 ng/mg creatinine. Suitably, the devices, methods and kits according to the present disclosure are configured to detect CEMA in the amount of 12 ng/mg creatinine. These amounts are diagnostic for abstainers of smoking and readings are taken in 24 hour urine after 5 days of the investigational period.

Suitably, the devices, methods and kits according to the present disclosure are configured to detect CEMA in the range of about 32 ng/ml to about 98 ng/ml or between about 7-17 ng/ml or between about 31 and 90 ng/ml or between about 5 to 12 ng/ml. Suitably, these values are determined in urine, suitably 24 hr urine.

Suitably, the devices, methods and kits according to the present disclosure are configured to visually display a result. The result can be determined using a machine or by eye. In certain embodiments, the result is determined by eye.

In certain embodiments, the result is determined by eye. In one embodiment, the devices, methods and kits and configured to visually display a result when a threshold level of CEMA that is greater than or equal to 10 pg/ml in 24 hour urine is crossed. In another embodiment, the devices, methods and kits and configured to visually display a result when a threshold level of CEMA that is greater than or equal to 20 pg/ml, 30 pg/ml, 40 pg/ml or 50 pg/ml in 24 hour urine is crossed.

Amounts of Metabolites

As described herein, the amounts of metabolites can be measured in order to decipher the smoking status of a subject using the data presented in Table 1 at, for example, day 5.

For example, if the amount of total NNAL in 24 hour urine is between about 37-115 pg/ml at day 5 of the investigational period and/or the amount of CEMA in 24 hour urine is between about 31-90 ng/ml at day 5 of the of the investigational period and/or the amount of cotinine in 24 hour urine is between about 456-1300 ng/ml at day 5 of the investigational period is indicative that the subject is a consumer of conventional cigarettes Baseline measurements are taken by allowing the subject to smoke their chosen brand of conventional cigarette for 2 days. After this 2 day period, the subject then elects to continue smoking conventional cigarettes, to switch to a smoke-free alternative or to abstain from smoking according to their preference. After 5 days of the investigational period, 24-hour urine is then collected to measure the level of metabolites therein.

By way of further example, if the amount of total NNAL in 24 hour urine is between about 17-40 pg/ml at day 5 of the investigational period and/or the amount of CEMA in 24 hour urine is between about 5-11 ng/ml at day 5 of the investigational period and/or the amount of cotinine in 24 hour urine is between about 10-42 ng/ml at day 5 of the investigational period is indicative that the subject is a consumer of smoke-free alternatives. Baseline measurements are taken by allowing the subject to smoke their chosen brand of conventional cigarette for 2 days. After this 2 day period, the subject then elects to continue smoking conventional cigarettes, to switch to a smoke-free alternative or to abstain from smoking according to their preference. After 5 days of the investigational period, 24-hour urine is then collected to measure the level of metabolites therein.

By way of further example, if the amount of total NNAL in 24 hour urine is between about 17-40 pg/ml at day 5 of the investigational period and/or the amount of CEMA in 24 hour urine is between about 4-15 ng/ml at day 5 of the investigational period and/or the amount of cotinine in 24 hour urine is between about 10-42 ng/ml at day 5 of the investigational period is indicative that the subject has abstained from smoking. Baseline measurements are taken by allowing the subject to smoke their chosen brand of conventional cigarette for 2 days.

After this 2 day period, the subject then elects to continue smoking conventional cigarettes, to switch to a smoke-free alternative or to abstain from smoking according to their preference. After 5 days of the investigational period, 24-hour urine is then collected to measure the level of metabolites therein.

In view of the amounts of the metabolites indicated above that are diagnostic for smoking status, the methods, devices and kits are configured such that these diagnostic levels can be measured. Suitably, the methods, devices and kits are configured such that these diagnostic levels can be measured in a quick and easy to use format. In certain embodiments, the methods, devices and kits are configured to indicate when the amount of total NNAL in 24 hour urine is between about 37-115 pg/ml at day 5 of the investigational period and/or the amount of CEMA in 24 hour urine is between about 31-90 ng/ml at day 5 of the of the investigational period and/or the amount of cotinine in 24 hour urine is between about 456-1300 ng/ml at day 5 of the investigational period as this will be diagnostic for the subject being a consumer of conventional cigarettes In certain embodiments, the methods, devices and kits are configured to give indicate when the amount of total NNAL in 24 hour urine is between about 17-40 pg/ml at day 5 of the investigational period and/or the amount of CEMA in 24 hour urine is between about 5-11 ng/ml at day 5 of the investigational period and/or the amount of cotinine in 24 hour urine is between about 10-42 ng/ml at day 5 of the investigational period is indicative that the subject is a consumer of smoke-free alternatives.

In certain embodiments, the methods, devices and kits are configured to indicate when the amount of total NNAL in 24 hour urine is between about 17-40 pg/ml at day 5 of the investigational period and/or the amount of CEMA in 24 hour urine is between about 4-15 ng/ml at day 5 of the investigational period and/or the amount of cotinine in 24 hour urine is between about 10-42 ng/ml at day 5 of the investigational period as this will be diagnostic for the subject having abstained from smoking.

In one exemplary assay format, three individual tests can be run corresponding to one test that is diagnostic for the subject being a consumer of conventional cigarettes, one test that is diagnostic for the subject being a consumer of smoke-free alternatives and one test being diagnostic for the subject having abstained from smoking. One exemplary test format is a portable lateral flow immunoassay device—such as a dipstick—in which the sample to be tested is challenged with three different portable lateral flow immunoassay devices, each configured to be diagnostic for each of the three different smoking statuses. In the alternative, all three tests can be integrated onto one portable lateral flow immunoassay device.

In a preferred embodiment, CEMA and cotinine can ensure a separation of conventional cigarette smokers and smoking abstainers after 2 days with a specificity and sensitivity of at least 75%.

At day 2, CEMA levels in conventional cigarette smokers is between about 32 ng/ml to about 98 ng/ml, suitably, in urine, more suitably 24 hr urine.

At day 2, cotinine levels in conventional cigarette smokers is between about 459 ng/ml to about 1350 ng/ml. Total NNAL provides the same level of discrimination between day 5 and day 30. Between day 5 and day 30, total NNAL levels in conventional cigarette smokers is between about 33 pg/ml to about 132 pg/ml, suitably, in urine, more suitably 24 hr urine.

At day 2, CEMA levels in smoking abstainers is between about 7-17 ng/ml suitably, in urine, more suitably 24 hr urine.

At day 2, cotinine levels in smoking abstainers is between about 339-959 ng/ml suitably, in urine, more suitably 24 hr urine.

Between day 5 and day 30, total NNAL levels in smoking abstainers is between about 2.5-46 pg/ml suitably, in urine, more suitably 24 hr urine.

Consumers of smoke-free alternatives can be distinguished from conventional cigarette smokers based on CEMA and total NNAL after day 5 with a specificity and sensitivity of at least 75%.

At day 5, CEMA levels in conventional cigarette smokers is between about 31 and 90 ng/ml, suitably, in urine, more suitably 24 hr urine.

At day 5, total NNAL levels in conventional cigarette smokers is between about 37 and 115 pg/ml, suitably, in urine, more suitably 24 hr urine.

At day 5, CEMA levels in consumers of smoke-free alternatives is between about 5 to 12 ng/ml, suitably, in urine, more suitably 24 hr urine.

At day 5, total NNAL levels in consumers of smoke-free alternatives is between about 17-41 pg/ml, suitably, in urine, more suitably 24 hr urine.

Consumers of smoke-free alternatives can be distinguished from smoking abstainers based on free Cotinine after 2 days (with a specificity and sensitivity of at least 75%).

At day 2, free cotinine in consumers of smoke-free alternatives is between about 546-1160 ng/ml, suitably, in urine, more suitably 24 hr urine.

At day 2, free cotinine in smoking abstainers is between about 128-313 ng/ml suitably, in urine, more suitably 24 hr urine.

In one embodiment, if the amount of cotinine is between about 10.6 and 41.5 ng/ml in 24 hour urine at day 5 of an investigational period is indicative of a smoking abstainer; and if the amount of total NNAL is between about 37.7 pg/ml and 115 pg/ml in 24 hour urine and the amount of CEMA is about 31.1 ng/ml and 90 ng/ml in 24 hour urine at day 5 of an investigational period is indicative of a subject exposed to combusted tobacco; and if the amount of cotinine is between about 652.5 and 1115 ng/ml ng/ml or more in 24 hour urine at day 5 of an investigational period is indicative of a subject exposed to heated tobacco.

Figure 2:
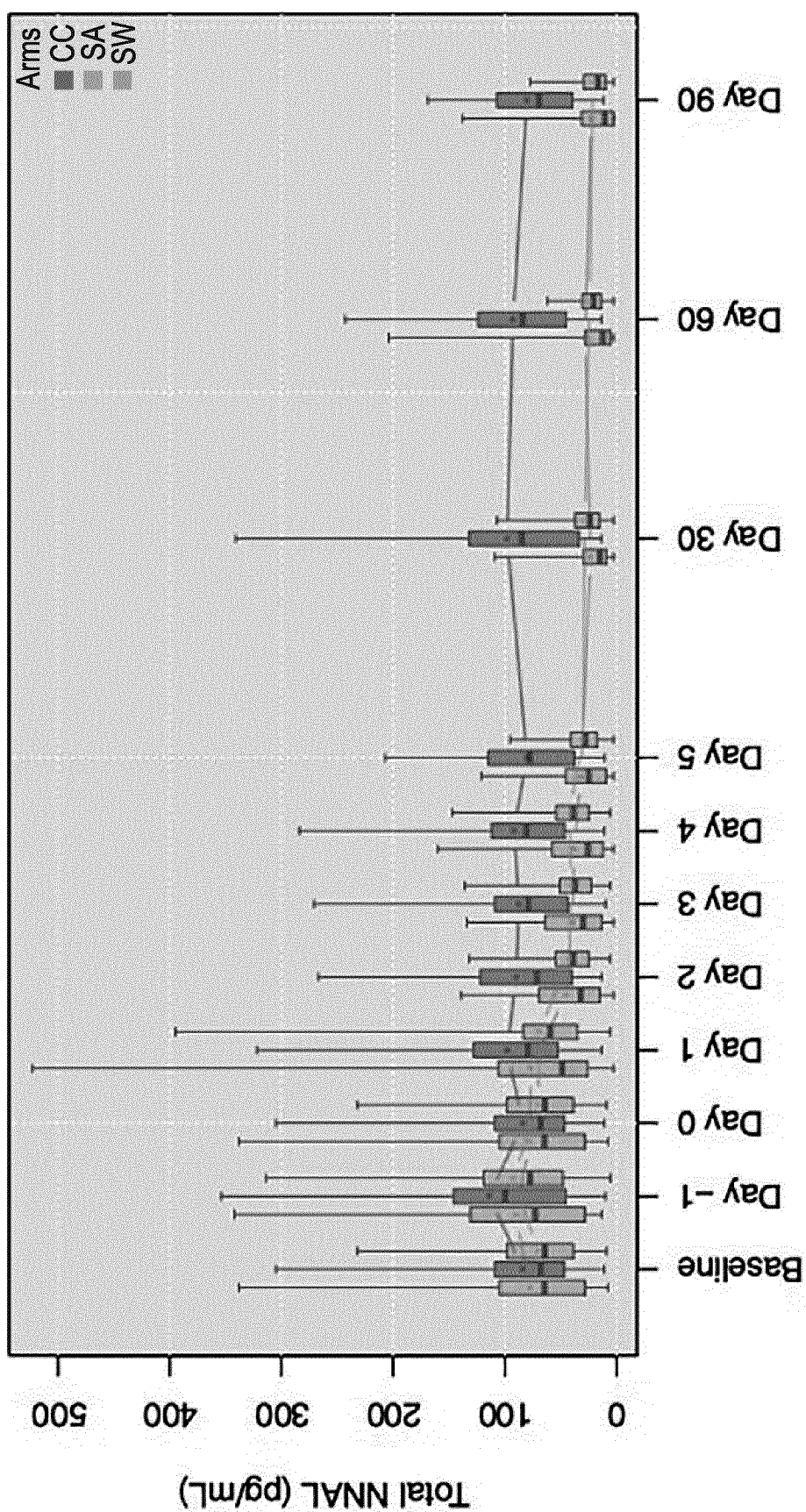
FIG. 2: Total NNAL: The bottom of the box is the first quartile (value below which 25% of the observations lie), the top is the third quartile (value below which 75% of the observations lie) and the middle bar is the median of the observations. The whiskers extend to the minimum observed value and maximum observed value respectively.
Figure 3:
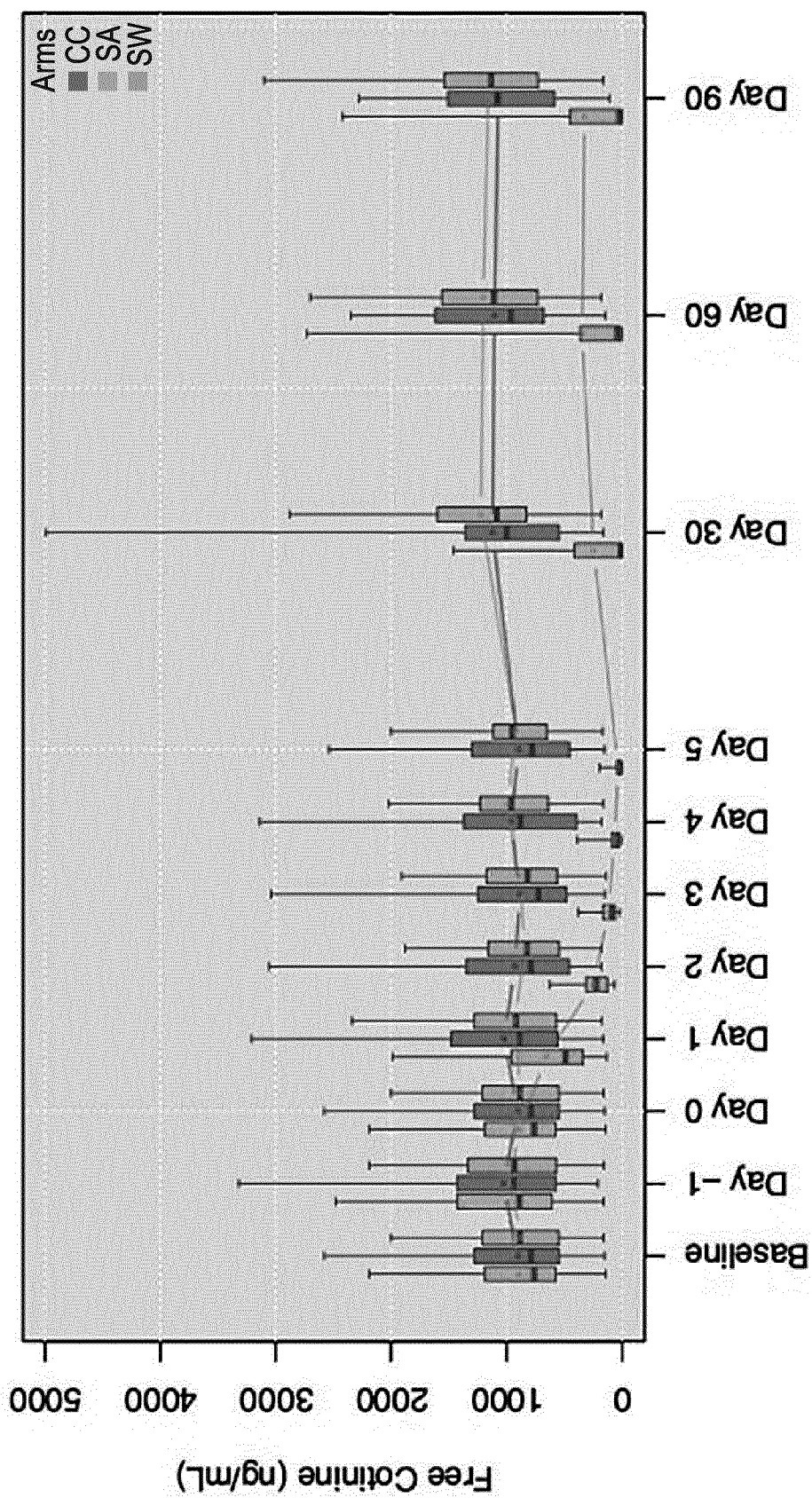
FIG. 3: Free Cotinine: The bottom of the box is the first quartile (value below which 25% of the observations lie), the top is the third quartile (value below which 75% of the observations lie) and the middle bar is the median of the observations. The whiskers extend to the minimum observed value and maximum observed value respectively.

These values can be appreciated from the data presented in Table 1 and FIGS. 1 to 3.

Reference Values of Metabolites

Reference values can be employed to compare the amounts of one or more metabolites detected in a subject against known reference values to reach a determination on the smoking status of the subject. A value above or below or the same as the reference value may be indicative that a threshold has been crossed. For example, a value above or below a baseline value may be indicative that a threshold has been crossed.

Compared to baseline, a −2.8% to 10.5% change (3.9% average increase) in total NNAL is indicative of a consumer of conventional cigarettes after 5 days of the investigational period in 24-hour urine.

Compared to baseline, a −57% to −51% change (−54% average decrease) in total NNAL is indicative of a consumer of smoke-free alternatives after 5 days of the investigational period in 24-hour urine.

Compared to baseline, a −67 to −61% decrease (−63.9% average decrease) in total NNAL is indicative of a smoking abstainer after 5 days of the investigational period in 24-hour urine.

Compared to baseline, a −4% to 12% change (4.2% average increase) in CEMA is indicative of a consumer of conventional cigarettes after 5 days of the investigational period in 24-hour urine.

Compared to baseline, a −87% to −85% change (−86% average decrease) in CEMA is indicative of a consumer of smoke-free alternatives after 5 days of the investigational period in 24-hour urine.

Compared to baseline, a −88 to −85% decrease (−86% average decrease) in CEMA is indicative of a smoking abstainer after 5 days of the investigational period in 24-hour urine.

Reference values may be established either within (i.e., constituting a step of) or external to (i.e., not constituting a step of) the methods and uses as taught herein. Accordingly, any one of the methods or uses taught herein may comprise a step of establishing a requisite reference value. Compared to baseline, a 1.5% to 18% decrease at day 2 for CEMA levels is indicative of a smoker of conventional cigarettes, suitably, in urine, more suitably 24 hr urine.

Compared to baseline, a 16% decrease to 6% increase at day 2 for free cotinine levels is indicative of a smoker of conventional suitably, in urine, more suitably 24 hr urine.

Compared to baseline, a 20% decrease to 6% increase at day 5 for total NNAL is indicative of a smoker of conventional cigarettes, suitably, in urine, more suitably 24 hr urine.

Compared to baseline, a 29% decrease to 17.5% increase at day 30 for total NNAL is indicative of a smoker of conventional cigarettes suitably, in urine, more suitably 24 hr urine.

Compared to baseline, a 79% to 80% decrease in CEMA levels at day 2 is indicative of a smoking abstainer, suitably, in urine, more suitably 24 hr urine.

Compared to baseline, a 74% to 78% decrease in cotinine levels at day 2 is indicative of a smoking abstainer, suitably, in urine, more suitably 24 hr urine.

Compared to baseline, a 56% to 67% decrease in total NNAL at day 5 is indicative of a smoking abstainer. Compared to baseline, a 68% to 72% decrease in total NNAL at day 30 is indicative of a smoking abstainer, suitably, in urine, more suitably 24 hr urine.

Compared to baseline, a 9.5% to 20.6% decrease in CEMA levels at day 5 is indicative of a consumer of conventional cigarettes, suitably, in urine, more suitably 24 hr urine.

Compared to baseline, a 19% decrease to 5% increase in total NNAL levels at day 5 is indicative of a consumer of conventional cigarette, suitably, in urine, more suitably 24 hr urine.

Compared to baseline, a 83% to 84% decrease in CEMA levels at day 5 is indicative of a consumer of smoke-free alternatives, suitably, in urine, more suitably 24 hr urine.

Compared to baseline, a 55% to 58% decrease in total NNAL levels at day 5 is indicative of a consumer of smoke-free alternatives, suitably, in urine, more suitably 24 hr urine.

Compared to baseline, a 74% to 77% decrease in free cotinine at day 2 is indicative of a smoking abstainer, suitably, in urine, more suitably 24 hr urine.

Compared to baseline, a 0.3% to 4% decrease in free cotinine at day 2 is indicative of a consumer of smoke-free alternatives, suitably, in urine, more suitably 24 hr urine.

Compared to baseline, a 74% to 78% decrease in free cotinine at day 2 is indicative of a smoking abstainer, suitably, in urine, more suitably 24 hr urine.

These values are calculated based on the data presented in Table 1 and FIGS. 1 to 3.

Normalization to Creatinine

In some embodiments, such as when a quantitative result is required and to provide a control for normal kidney function, the method of the invention can include creatinine measurements, and the values of the metabolites—such as NNAL and CEMA—are normalized to urinary creatinine. Such normalization is not required for a semi-quantitative or qualitative test. Since a portable lateral flow immunoassay device—such as a dipstick—is typically reporting a semi-quantitative or qualitative result then normalization to creatinine will not be required in these embodiments of the disclosure. Moreover, even when a quantitative result is required, the use of a creatinine control is not always critical or essential because reference values for creatinine in urine samples have been derived (see, for example, Occupational Medicine (2011), volume 61, issue 5, pages 349-353).

Detecting Metabolites

The amount or quantity or levels of metabolite(s) may be measured by any suitable technique—such as may be known in the art and described herein. For example, one may employ binding agents capable of specifically binding to the respective metabolites. Binding agents may be inter alia an antibody or a fragment thereof, aptamer, affimer, photoaptamer, protein, peptide, peptidomimetic or a small molecule. For instance, one may employ an immunoassay technology or a mass spectrometry analysis method or a chromatography method, or a combination of said methods.

In certain embodiments, the presence and/or quantity of any one or more metabolites may be measured using an immunoassay technology. Various kinds of immunoassay technology are known in the art. In one format, the metabolite(s) can be conjugated to a labeled detection reagent and compete to specifically bind to a specific binding agent. The presence or absence of the metabolite(s) in the sample is measured, respectively, by the absence or presence of a visible (or measurable) signal. In another format, a labeled detection reagent binds to the metabolite(s) forming a complex, and the complex is immobilised on the solid support via a specific binding agent. The presence or absence of the metabolite(s) in the liquid sample is measured by the presence or absence of a visible (or measurable) signal.

Various devices are well known in the art and are further described herein. Such devices are commonly suitable for single and domestic use because they are easy and quick to use and the results can be visualised using the naked eye.

In some circumstances, more complex devices may be required for determining the presence and/or quantity of the metabolite(s), for example, when interpretation with the naked eye is either not possible or creates uncertainty. Such devices can include a receptacle adapted for receiving an immunochromatographic device, an imaging device adapted to acquire at least one digital image of the revealing zone of the device, a processor adapted to process the at least one digital image and means for reporting the result of the qualitative and/or quantitative evaluation. Such a device is described in WO2016/075405 wherein there is disclosed a system for the qualitative and/or quantitative evaluation of at least one metabolite likely to be contained in a liquid sample deposited on an immunochromatographic device. The evaluation system comprises a reading device and an analysis device that can be structurally separate from one another. The reading device comprises a receptacle adapted to receive the immunochromatographic device, and an imaging device for acquiring at least one digital image of its display area. The analysis device can further comprise a processor adapted to process the at least one digital image, and which is suitable for the qualitative and/or quantitative evaluation of the at least one metabolite that may be contained in the liquid sample. The analysis device may further comprise means for outputting the result of the evaluation. The evaluation system can further comprise a device adapted to transmit the at least one digital image acquired from the reading device to a remote analysis device, for example, via a telecommunications network. The reading device can be a portable device. The imaging device can comprise an optical (or photographic) sensor, an analog-to-digital converter, and a processing module, comprising a processor and a computer program which can be adapted to generate a digital image from the data coming from the converter. The optical sensor can be a photosensitive electronic component for converting electromagnetic radiation into an analog electrical signal. The signal that is obtained can be digitised by the analog-digital converter and then processed by the processing module to obtain a digital image corresponding to the revelation zone of the immunochromatographic device. The device adapted to transmit the at least one digital image can comprise wired or wireless means that is capable of transmitting at least one digital image from the reading device. The digital image acquired by the reading device can be transmitted to a remote analysis device—such as a dedicated computer server. In operation, the reading device can be paired with the transmission device to allow data exchange there between. A sample to be analysed can be deposited on to an immunochromatographic device and incubated for a sufficient period of time. The reading device can then acquire a digital image from the immunochromatographic device for transmission to the transmission device. The digital image can then be transmitted by the transmitting device to the analysis device. Each digital image that is received by the analysis device can be processed for analysis.

In non-limiting examples, the immunoassay technology uses enzyme-linked immunosorbent assay (ELISA), radio-immunoassay (RIA), fluorescent immunoassay, chemiluminescent immunoassay, DRI immunoassay, quantitative immunoassy, lateral flow immunoassay, microfluidic immunoassay and agglutination immunoassay technologies, preferably using ELISA. In one embodiment the use of lateral flow immunoassay is preferred. In another embodiment the use of competitive format lateral flow immunoassay is preferred.

Alternatively, or in addition, the presence and/or quantity of any one or more metabolites as taught herein may be measured using techniques that are antibody- or chromatography-based, using competitive binding assays and/or using derivatising and/or colourant-bearing agents. In preferred embodiments, the presence and/or quantity of any one or more metabolites as taught herein may be measured using a binding agent capable of specifically binding to the respective markers, in preferred but non-limiting examples, using an aptamer, antibody or a fragment thereof, affimer, photoaptamer, protein, peptide, peptidomimetic, or a small molecule, preferably using an aptamer, affimer or antibody, more preferably using an antibody or a fragment thereof or affimer.

Binding Agent

Suitably the specific binding agent may bind to its intended target(s) with affinity constant ($K_A$) of such binding $K_A \geq 1\times10^6$ $M^{-1}$, more preferably $K_A \geq 1\times10^7$ $M^{-1}$, yet more suitably $K_A \geq 1\times10^8$ $M^{-1}$, even more suitably $K_A \geq 1\times10^9$ $M^{-1}$, and still more suitably $K_A \geq 1\times10^{10}$ $M^{-1}$ or $K_A \geq 1\times10^{11}$ $M^{-1}$, wherein $K_A$=[SBA_T]/[SBA][T], SBA denotes the specific-binding agent, T denotes the intended target. Determination of $K_A$ may be carried out by methods known in the art, such as for example, using equilibrium dialysis and Scatchard plot analysis.

Antibodies

Antibodies can be used to detect one or more of the metabolites described herein. An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibodies may be antibody fragments. "Antibody fragments" comprise a portion of an intact antibody, comprising the antigen-binding or variable region thereof. Examples of antibody fragments include Fab, Fab', F(ab')2, Fv and scFv fragments; diabodies; linear antibodies; single-chain antibody molecules; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromadenus*), llama (e.g., *Lama paccos, Lama glama* or *Lama vicugna*) or horse.

A skilled person will understand that an antibody may include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polydonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The binding molecule may be labelled with a tag that permits detection with another agent (e.g. with a probe binding partner). Such tags can be, for example, biotin, streptavidin, his-tag, myc tag, maltose, maltose binding protein or any other kind of tag known in the art that has a binding partner. Example of associations which can be utilised in the probe:binding partner arrangement may be any, and includes, for example biotin:streptavidin, his-tag/metal ion (e.g. $Ni^{2+}$), maltose/maltose binding protein.

The binding molecule or binding molecule conjugate may be associated with or attached to a detection agent to facilitate detection. Examples of lab detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. More commonly, the detection agent is a particle. Examples of particles useful in the practice of the invention include, but are not limited to, colloidal gold particles; colloidal sulphur particles; colloidal selenium particles; colloidal barium sulphate particles; colloidal iron sulphate particles; metal iodate particles; silver halide particles; silica particles; colloidal metal (hydrous) oxide particles; colloidal metal sulphide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles are colloidal gold particles. Colloidal gold may be made by any conventional means, such as the methods outlined in G. Frens, 1973 Nature Physical Science, 241:20 (1973). Alternative methods may be described in U.S. Pat. Nos. 5,578,577, 5,141,850; 4,775,636; 4,853,335; 4,859,612; 5,079,172; 5,202,267; 5,514,602; 5,616,467; 5,681,775.

Anti-CEMA Antibodies

As discussed herein, CEMA can be detected using an antibody—such as a monoclonal antibody—or a fragment thereof, which specifically binds to CEMA, optionally bound to an immunogenic carrier. For example, the methods described herein or in WO2009/010296 can be employed. A further aspect relates to a conjugate comprising CEMA coupled to an immunogenic carrier. There is also disclosed a conjugated obtainable by coupling CEMA to an immunogenic carrier. The immunogenic carrier can be, for example, a protein, a peptide, an oligonucleotide or a polymer. A method for the preparation of the conjugate is also disclosed, comprising: (a) activating the immunogenic carrier; and (b) coupling the activated immunogenic carrier obtained in step a) to CEMA. A further aspect of the present disclosure relates to an anti-CEMA antibody or a fragment thereof capable of specifically binding to CEMA. There is also disclosed a method for producing this antibody or the fragment thereof, comprising immunizing a non-human animal with the conjugate described herein. A pharmaceutical composition comprising the conjugate is also disclosed as is a method of detecting CEMA in a sample comprising subjecting the sample to the anti-CEMA antibody or a fragment thereof and detecting binding of the antibody or the fragment thereof to CEMA.

Binding is indicative of the presence of CEMA in the sample. There is also described a method for the detection of antibodies or fragments thereof specific for CEMA comprising subjecting a sample from a subject to the conjugate described herein and detecting binding of the conjugate to the antibody or the fragment thereof.

One method for raising anti-CEMA antibodies involves the use of hybridomas. Pathogen-free BALB/c mice can be primed with a CEMA conjuagate using complete Freund's adjuvant (Sigma). Mice can be boosted by gastric intubation on day 14, 16, 28, 30, 42 and 44 with the same dose of antigen in the presence of cholera toxin (Sigma). Sera can be drawn on day 0, 14, 28, 42, 55 and 84 and anti-CEMA antibody titer can be measured by direct ELISA.

Three days prior to hybridoma fusion, a final boost can be performed with incomplete Freund's adjuvant (Sigma) to mice with the highest CEMA-specific antibody titers.

Hybridomas can be produced using ClonaCell™-HY complete kit (StemCell Technologies).

Briefly, from immunized mice spleen, splenocytes are washed and incubated in PEG-containing medium with parental myeloma cells. After a 24 hour expansion, cells are mixed with a methylcellulose-based HAT (hypoxanthine, aminopterin and thymine) selective medium for hybridomas. The mixture is plated on dishes and incubated at 37° C., allowing fused cells to growth for 14 days. Hybridoma colonies can then be picked and transferred into 96-well plates with growth medium. After 4 days of growth at 37° C., each supernatant can be tested for the presence of specific [NNK-C2]-antibodies by direct ELISA. Positive clones were further adapted to RPMI-1640 medium supplemented with HyClone HyQ PF-Mab (Perbio Sciences), a protein-free nutrient supplement for mAb production.

Detection

Any existing, available or conventional separation, detection and quantification methods may be used herein to determine or detect or measure the presence or absence (e.g., readout being present vs. absent; or detectable amount vs. undetectable amount) and/or quantity (e.g., readout being an absolute or relative quantity, such as, for example, absolute or relative concentration) of metabolites thereof in samples (any molecules or analytes of interest to be so-measured in samples, including any one or more metabolites as taught herein, may be herein below referred to collectively as metabolites).

For example, such methods may include biochemical assay methods, immunoassay methods, competitive binding assays, sandwich binding assays, mass spectrometry analysis methods, or chromatography methods, or combinations thereof.

Competitive Binding Assays and Immunoassays

Competitive binding assays and immunoassays can be used to detect one or more of the metabolites described herein. These methods known as such for detecting one or more metabolites of interest in a sample, wherein specificity of an assay for metabolites of interest is conferred by specific binding between a specific-binding agent, commonly an antibody, and the metabolites of interest. Quantitative assays are used to measure the amount of specific moieties in a biologic matrix such as plasma or serum. Immunoassay technologies include without limitation direct ELISA (enzyme-linked immunosorbent assay), indirect ELISA, sandwich ELISA, competitive ELISA, multiplex ELISA, radioimmunoassay (RIA) technologies, and other similar techniques known in the art. Principles of these immunoassay methods are known in the art, for example John R. Crowther, "The ELISA Guidebook", 1st ed., Humana Press 2000, ISBN 0896037282.

By means of further explanation and not limitation, direct ELISA employs a labelled primary antibody or a fragment thereof to bind to and thereby quantify target antigen in a sample immobilised on a solid support such as a microwell plate. Indirect ELISA uses a non-labelled primary antibody which binds to the target antigen and a secondary labelled antibody that recognises and allows to quantify the antigen-bound primary antibody. In sandwich ELISA, the target antigen is captured from a sample using an immobilised 'capture' antibody which binds to one antigenic site within the antigen and, subsequent to removal of non-bound metabolites, the so-captured antigen is detected using a 'detection' antibody which binds to another antigenic site within said antigen, where the detection antibody may be directly labelled or indirectly detectable as above. Competitive ELISA uses a labelled 'competitor' that may either be the primary antibody or the target antigen. In an example, non-labelled immobilised primary antibody is incubated with a sample, this reaction is allowed to reach equilibrium and then labelled target antigen is added. The latter will bind to the primary antibody wherever its binding sites are not yet occupied by non-labelled target antigen from the sample. Thus, the detected amount of bound labelled antigen inversely correlates with the amount of non-labelled antigen in the sample. Multiplex ELISA allows simultaneous detection of two or more metabolites within a single compartment (e.g., microplate well) usually at a plurality of array addresses (see, for example, Nielsen & Geierstanger 2004. J Immunol Methods 290: 107-20 and Ling et al. 2007. Expert Rev Mol Diagn 7: 87-98 for further guidance). As appreciated, labelling in ELISA technologies is usually by enzyme (such as, e.g., horse-radish peroxidase) conjugation and the end-point is typically colourimetric, chemiluminescent or fluorescent, magnetic, piezo electric, pyroelectric and other.

Radioimmunoassay

Radioimmunoassay (RIA) can be used to detect one or more of the metabolites described herein. This is a competition-based technique and involves mixing known quantities of radioactively-labelled (e.g., $^{125}$I- or $^{131}$I-labelled) target antigen with antibody or a fragment thereof to said antigen, then adding non-labelled or 'cold' antigen from a sample and measuring the amount of labelled antigen displaced (see, e.g., "An Introduction to Radioimmunoassay and Related Techniques", by Chard T, ed., Elsevier Science 1995, ISBN 0444821198 for guidance).

Microfluidic Systems

Microfluidic systems can be used to detect one or more of the metabolites described herein. They are fabricated by microelectromechanical systems (MEMS) technology and are usually referred to as "lab-on-a-chip" (LOC), "biochips," or "micro-total-analysis-system." They are often envisioned as miniaturised versions of their large-scale counterparts. These miniaturised systems are able to carry out entire protocols traditionally performed in a laboratory. Sample pretreatment, sample/reagent transport, mixing, reaction, separation, detection, and product collection can all be performed automatically on a single LOC system. Functional microfluidic devices, such as micropumps, microvalves, microfilters, microreactors, and microseparators may be microfabricated and even integrated to perform a specific assay. The advantages of these developed LOC systems include less sample/reagent consumption, a reduced risk of contamination, enhanced sensitivity, less unit cost, lower power consumption, and a higher reliability and functionality. More importantly, portability arising from their compact form is a key factor for point-of-care (POC) applications.

Agglutination Immunoassays

Agglutination immunoassays can be used to detect one or more of the metabolites described herein. They utilise the binding and agglutination (clumping) of antibodies or fragments thereof to antigen-DNA conjugates, enabling ligation of the DNA strands and subsequent quantification by methods including quantitative polymerase chain reaction (qPCR).

Agglutination-PCR (ADAP) is an ultrasensitive solution-phase method for detecting such antibody binding. Like other Immuno-PCR (IPCR) detection methods ADAP combines the specificity of antibody-antigen recognition and the sensitivity of PCR. ADAP detects zepto- to attomoles of antibodies in 2 µl of sample with a dynamic range spanning 5-6 orders of magnitude. For example, ADAP allows to detect anti-thyroglobulin autoantibodies from human patient plasma with a 1000-fold increased sensitivity over an FDA-approved radioimmunoassay. ADAP also allows to simultaneously detect multiple antibodies in one experiment.

DRI Technology

DRI technology can be used to detect one or more of the metabolites described herein. An example of DRI technology is that offered by Thermo Scientific™ and is based on the competition between a drug or drug metabolite labelled with the enzyme glucose-6-phosphate dehydrogenase (G6PDH) and free drug from the sample for a fixed amount of specific antibody binding sites. In the absence of free drug from the sample, the specific antibody binds to the drug labelled with G6PDH. As a result, enzyme activity is inhibited. If the drug is present in the sample, it competes with the enzyme-drug conjugate for the limited number of antibody binding sites, resulting in more active enzyme. This phenomenon creates a direct relationship between the drug concentration in the urine and the enzyme activity. The enzyme G6PDH activity is determined spectrophotometrically at 340 nm by measuring its ability to convert nicotinamide adenine dinucleotide (NAD) to NADH.

Immunochromatography

Immunochromatography can be used to detect one or more of the metabolites described herein and is a preferred detection method of this disclosure. This is also known as a lateral flow immunochromatographic assay. Immunochromatography can be integrated into simple devices intended to detect the presence (or absence) of an analyte in a sample—such as urine—without the need for specialised and costly equipment. Immunochromatography can also be integrated into portable lateral flow immunoassay devices, as discussed below. The general principle of immunochromatography is based on a liquid sample containing the metabolite(s) to be detected moving by capillary action without the assistance of external forces through various zones of a lateral flow test strip. The lateral flow test strip can be a polymeric strip, on which molecules that can interact with the metabolite(s) are attached. A typical lateral flow test strip consists of overlapping membranes that are mounted on a backing card for stability and handling. Such a lateral flow test strip can comprise one or more porous elements which when wetted with the sample, provide a visual change in the presence of metabolite(s) and/or indicate the concentration of the metabolite(s) in said sample. The sample is applied to one end of the strip, on an adsorbent sample pad and migrates through the lateral flow test strip. The adjacent porous element is a conjugate pad, which typically contains specific binding agents that are specific to the metabolite(s) being detected and are labelled. Together they can form a labeled specific binding agent-metabolite conjugate. Methods for associating or attaching the label to the specific binding agent are well known in the art and described in, for example, EP007654. The conjugate migrates along the strip into the next adjacent porous element called the detection zone.

This is a porous membrane—such as nitrocellulose—with specific biological components—such as specific binding agents immobilised thereon that are configured to bind the metabolite(s) present in the conjugate. Suitably, this occurs in one or more test lines of the detection zone. Recognition of the metabolite(s) produces a response on the test line(s) in the detection zone. The results, represented by the test lines can be assessed by eye or using a dedicated reader. The liquid flows across the lateral flow test strip because of the capillary force of the strip material and, to maintain this movement, a further porous element adjacent to the detection zone is optionally present, called an absorption pad. This is located at the end of the strip to wick the excess reagents and prevent backflow of the liquid.

In order to test multiple metabolites simultaneously under the same conditions, additional test lines containing specific binding agents to different metabolites can be immobilised in an array format. Such a configuration is of particular use in the present disclosure as more than metabolite is detected.

In further detail, the lateral flow test strip generally comprises (i) a sample pad; (ii) a conjugate pad; (iii) a detection zone; and (iv) an optional absorption pad. The sample pad and optional absorption pad are located at opposing ends of the lateral flow test strip.

Typically, the conjugate pad is adjacent the sample pad, the detection zone is adjacent the conjugate pad and the optional absorption pad is adjacent the detection zone.

The first element of the lateral flow test strip is a porous element for the sample which is referred to herein as the sample pad. This acts as a sponge and holds an excess of sample fluid. It is typically made of cellulose or glass fiber or a combination thereof. Its function is to transport the sample to other components of the lateral flow test strip. The sample pad should be capable of transportation of the sample in a smooth, continuous and homogenous manner. The sample pad can be impregnated with solutions—such as buffer salts and surfactants—as required. Once soaked, the fluid migrates to the second element of the lateral flow test strip.

The second element of the lateral flow test strip is a porous element for conjugate and is referred to herein as a conjugate pad. This is where labeled specific binding agent(s) each capable of individually binding the metabolites (or in certain assay formats, metabolite analogues) is present. Glass fiber, cellulose and polyesters are typical examples of materials used to make the conjugate pad. The labeled specific binding agent can be present in a dried format in a matrix, for example, a salt-sugar matrix, in the conjugate pad.

The labeled specific binding agent can be a labeled antibody or a fragment thereof or an aptamer or an affimer or the like. At least two different specific binding agents (for example, three specific binding agents) will normally be used to detect each of the metabolites described herein. The amounts thereof can be adjusted as required to fine-tune the sensitivity of the assay for each metabolite. Typically, the amount of each specific binding agent that is used will be different. The specific binding agents can be labelled with the same or a different label, as required. The sample fluid solubilises the specific binding agent(s) and in one combined transport action the sample and specific binding agent(s) mix while flowing through the conjugate pad to form the labeled specific binding agent-metabolite conjugate.

In one embodiment, the conjugate pad comprises or consists of labelled specific binding agents each capable of individually binding: (i) cotinine and NNAL; or (ii) cotinine and CEMA; or (iii) cotinine and NNAL and CEMA, suitably, wherein each of the labelled specific binding agents is an antibody or fragment thereof, an aptamer, a photoaptamer, an affimer, a protein, a peptide, a peptidomimetic or a small molecule.

The lateral flow test strip will have one or more detection zones—such as test lines—where another molecule(s) is immobilised. Typically, the detection zone will be a nitrocellulose membrane. Typically, there will be at least two test lines which each contain a specific binding agent that is capable of capturing the labeled specific binding agent-metabolite conjugate or competes for binding. An optional control line can also be included. The exact configuration of the detection zone will depend upon the format of the assay—such as the sandwich or competitive format of the assay, as described below.

In one aspect, there is a disclosed a device for determining the smoking status of a subject, wherein said device comprises a plurality of different specific binding molecules deposited onto a solid phase to detect the presence of two or three tobacco smoke exposure biomarkers in a biological sample, said tobacco smoke exposure biomarkers consisting of: (i) cotinine and total 4-(methylnitrosamino)-1-(3-pyridyl)-1-butanol (NNAL); or (ii) cotinine and N-acetyl-S-[2-carboxyethyl]-L-cysteine (CEMA); or (iii) cotinine and NNAL and CEMA. The device can be configured for use in a sandwich format or competitive format. In certain embodiments, the use of the competitive format is preferred.

In the sandwich format assay, as the sample migrates it first encounters the conjugate pad.

If the metabolite(s) is present in the sample, the specific binding agent(s) in the conjugate pad bind to the metabolite(s) to form the labeled specific binding agent-metabolite conjugate which migrates and subsequently reaches the detection zone. The detection zone also contains specific binding agent(s) to the metabolite(s). Once the sample reaches the detection zone the labeled specific binding agent-metabolite conjugate can be captured by a specific binding agent to the metabolite but at a different site or epitope relative to the site or epitope to which the specific binding agent from the conjugate pad is bound. Metabolite becomes sandwiched between antibodies forming a complex. This results in a visual change, normally a line appearing, allowing the test to be read that a threshold has been crossed. The majority of sandwich assays also have a control line which will appear regardless of whether or not the metabolite(s) is present. Excess labeled antibody can be captured by secondary antibody, if required.

In one embodiment of the device configured for use in the sandwich format, (a) the conjugate pad comprises or consists of labeled specific binding agents deposited thereon each capable of individually binding the metabolites: (i) cotinine and NNAL; or (ii) cotinine and CEMA; or (iii) cotinine and NNAL and CEMA, and capable of forming labeled specific binding agent metabolite conjugates; and (b) the detection zone comprises or consists of immobilised specific binding agents each capable of individually binding to the metabolites.

In one exemplary format, non-visible indication of (i) cotinine and NNAL; or (ii) cotinine and CEMA; or (iii) cotinine and NNAL and CEMA on a test line(s) of the device indicates that the threshold of detection has not been crossed and is indicative of a non-smoking subject; visible indication of (i) cotinine and NNAL; or (ii) cotinine and CEMA; or (iii) cotinine and NNAL and CEMA on the test line(s) of the device indicates that the threshold of detection has been crossed and non-visible indication of (i) cotinine and NNAL; or (ii) cotinine and CEMA; or (iii) cotinine and NNAL and CEMA on the test line(s) of the device indicates that the threshold of detection has not been crossed and is indicative of a subject exposed to heated tobacco; and visible indication of (i) cotinine and NNAL; or (ii) cotinine and CEMA; or (iii) cotinine and NNAL and CEMA on the test line(s) of the device indicates that the threshold of detection has been crossed and is indicative of a subject exposed to combusted tobacco. A device can be configured such that the test line(s) are configured to indicate these results using the data presented in Table 1 for, example, using the day 5 results.

In the competitive format, as a sample migrates within the device, it first encounters the conjugate pad which contains labelled conjugates, i.e., labelled metabolite(s) or labelled analogue of the metabolite(s). Typically, the label is associated or attached to the metabolite(s) or analogue thereof through the use of a specific binding agent—such as an antibody or fragment thereof. The labelled conjugates become solubilised in the presence of the sample to form a mixture of metabolite(s) contained in the sample, and the labelled metabolite(s) or analogues thereof.

At the detection zone, another specific binding agent—to the metabolite(s) is immobilised forming a test line. When the migrating sample fluid flows into the detection zone, competition takes place between the sample metabolite(s) and the labelled conjugates for binding to the immobilised specific binding agent. The immobilized specific binding agent in the detection zone binds to a different site on the metabolite relative to the site to which the labelled specific binding agent is bound.

In one embodiment of the device configured for use in the competitive format: (a) the conjugate pad comprises or consists of labelled metabolite(s) deposited thereon, said labelled metabolite(s) consisting of: (i) labelled cotinine or an analogue thereof and labelled NNAL or an analogue thereof; or (ii) labelled cotinine or an analogue thereof and labelled CEMA or an analogue thereof; or (iii) labelled cotinine or an analogue thereof and labelled NNAL or an analogue thereof and labelled CEMA or an analogue thereof; and (b) the detection zone comprises or consists of immobilised specific binding agents each capable of individually binding: (i) the labelled cotinine or the analogue thereof and the labelled NNAL or the analogue thereof and cotinine and NNAL that may present in a sample; or (ii) the labelled cotinine or the analogue thereof and the labelled CEMA or the analogue thereof and cotinine and CEMA that may be present in a sample; or (iii) the labelled cotinine or the analogue thereof and the labelled NNAL or the analogue thereof and the labelled CEMA or the analogue thereof and cotinine and NNAL and CEMA that may be present in a sample.

In one exemplary embodiment of the competitive format, (i) visible indication of (i) cotinine and NNAL; or (ii) cotinine and CEMA; or (iii) cotinine and NNAL and CEMA on a test line(s) of the device indicates that the threshold of detection has not been crossed and is indicative of a non-smoking subject; (ii) no visible indication of (i) cotinine and NNAL; or (ii) cotinine and CEMA; or (iii) cotinine and NNAL and CEMA on a test line(s) of the device indicates that the threshold of detection has been crossed and visible indication of (i) cotinine and NNAL; or (ii) cotinine and CEMA; or (iii) cotinine and NNAL and CEMA on a test line(s) of the device indicates that the threshold of detection has not been crossed and is indicative of a subject exposed to heated tobacco; and (iii) no visible indication of (i) cotinine and NNAL; or (ii) cotinine and CEMA; or (iii) cotinine and NNAL and CEMA on a test line(s) of the device indicates that the threshold of detection has been crossed and is indicative of a subject exposed to combusted tobacco. A device can be configured such that the test line(s) are configured to indicate these results using the data presented in Table 1 for, example, using the day 5 results. This competitive format generally suits low molecular weight compounds which cannot bind two specific binding agents simultaneously. Absence of a signal at a test line is an indication of the presence of metabolite while appearance of signal indicates a negative result. In certain embodiments, the competitive format is preferred for use in the present disclosure.

A multiplex format can also be used when detecting more than one metabolite with a single strip. The multiplex detection format can be built in various ways, for example, by increasing the length of the lateral flow test strip or the length of the detection zone. The multiplex format can be used with the sandwich or competitive formats. In certain embodiments, a multiplex competitive format is preferred.

After passing through the conjugate pad and the detection zones, the fluid can enter the final porous element, which is referred to herein as the absorption pad. This functions as a waste container and is an optional feature.

The various parts of the lateral flow test strip are fixed or mounted over a backing card which serves as a support and makes it easier to handle the strip.

To obtain a qualitative or semi-quantitative result in which a signal is formed once the level of the metabolite(s) in the sample is higher than a certain predetermined threshold level or reference value or baseline value, a predetermined amount of fixed specific binding agent(s) may be present in the detection zone. This enables the capture of a certain amount of the metabolite(s) present in the sample, corresponding to the threshold level or value as predetermined. The remaining amount of metabolite(s) (if any) that is bound may then be allowed to further migrate to an optional further detection zone, which subsequently only produces a detectable signal if the level of the metabolite(s) in the sample is higher than the predetermined threshold level or value.

Depending on the assay format, the intensity of the colour or signal may can be compared to a reference colour or signal chart. Alternatively, the amount or intensity of the colour or signal may be measured with an electronic device comprising e.g. a light absorbance sensor or light emission meter, resulting in a numerical value of signal intensity or colour absorbance formed. This embodiment can be of particular relevance for monitoring the level of said metabolite(s) in a subject over a period of time.

In a further embodiment, the intensity of the colour or signal at the detection zone may either be compared to a reference colour or signal chart indicating that when the intensity of the signal is above or below a certain threshold signal, and indicating that the test is positive.

Alternatively, as discussed above, the amount or intensity of the colour or signal may be measured with an electronic device resulting in a numerical value of signal intensity or colour absorbance formed, which may then be displayed to the subject in the form of a negative result or a positive result.

The typical steps in carrying out immunochromatography are: (a) the preparation of labeled specific binding agent and capture of labelled specific binding agent against metabolite(s); (b) depositing the labeled specific binding agent onto the conjugate pad of the lateral flow test strip, and immobilizing the specific binding agent onto the detection zone of the lateral flow test strip; (iii) assembling the components onto the lateral flow test strip; (iv) adding the sample to be tested to the sample pad, together with an optional buffer; (v) waiting for the sample to flow through the lateral flow test strip and; (vi) read the result at the detection zone.

The lateral flow test strip can be configured to detect total NNAL or CEMA, and cotinine or it can be configured to detect total NNAL and CEMA and cotinine. The lateral flow test strip can be configured to include a positive control to demonstrate that the test works for subjects who do not have any tobacco metabolite in their urine (using, for example, creatine, albumin or a urine specific protein—such as Tamm-Horsfall protein (THP) as a marker(s)). Thus, in another embodiment, the lateral flow test strip is configured to detect total NNAL or CEMA, and cotinine and a positive control or it can be configured to detect total NNAL and CEMA and cotinine and a positive control.

The lateral flow test strip can be used directly as a device or it can be integrated into a housing, as required. Thus, there is also disclosed a device comprising the lateral flow test strip.

Most immunochromatographic tests operate on a purely qualitative basis. However, it is possible to measure the intensity of the detection zone to determine the quantity of metabolite in the sample. Handheld diagnostic devices known as lateral flow readers are used by several companies to provide a fully quantitative assay result. By utilising unique wavelengths of light for illumination in conjunction with either CMOS (complementary metal-oxide-semiconductor) or CCD (charge-coupled device) detection technology, a signal rich image may be produced of the actual test lines. Using image processing algorithms specifically designed for a particular test type and medium, test line intensities may then be correlated with analyte concentrations. One such handheld lateral flow device platform is made by Detekt Biomedical LLC. Alternative non-optical techniques are also able to report quantitative assays results. One such example is a magnetic immunoassay (MIA). Reducing variations in the capillary pumping of the sample fluid is another approach to move from qualitative to quantitative results.

Antibodies and fragments thereof, as described herein, are commonly used as specific binding agents in the detection zone where they specifically bind to metabolite through immunochemical interactions. Aptamers or affimers are sometimes preferred over antibodies due to their ease of manufacture, simple labelling, enhanced stability, enhanced reproducibility and enhanced versatility.

The specific binding agents are labelled and a wide variety of such labels are well known in the art. They can include gold nanoparticles, selenium nanoparticles, quantum dots, coloured latex beads, magnetic particles, carbon nanoparticles, silver nanoparticles, up converting phosphors, organic fluorophores, textile dyes, liposomes and enzymes. Colloidal gold nanoparticles are one of the most commonly used labels. Colloidal gold is inert and produces near perfect spherical particles. These particles have very high affinity toward biomolecules and can be easily functionalised. The optical properties of gold nanoparticles typically enhance sensitivity. The optical signal of gold nanoparticles can be amplified by deposition of silver, gold nanoparticles and enzymes, if required. When using gold nanoparticles, qualitative or semi-quantitative analysis can be carried out by visual inspection of the detection zone. A major advantage of visual inspection is that rapid qualitative answers can be obtained which simplifies the use of the device and allows for an immediate decision. For quantification, optical strip readers can be used.

Additional information about practical immunochromatography can be found in the handbook "Lateral flow immunochromatography assays" by P. J. Davies et al. published on 15 Mar. 2008 by Wiley Online Library.

Portable Lateral Flow Immunoassay Device

In another embodiment, the disclosure provides a portable lateral flow immunoassay device—such as a dipstick—to detect one or more of the metabolites described herein. The device can use the principles of immunochromatography and can comprise or consist of the lateral flow test strip as discussed above.

A lateral flow test strip for use in a sandwich format portable lateral flow immunoassay device according to one aspect of the present disclosure is now described. The lateral flow test strip comprises (i) a sample pad; (ii) a conjugate pad; (iii) a detection zone; and (iv) an optional absorption pad. The sample pad and optional absorption pad are located at opposing ends of the lateral flow test strip. Typically, the conjugate pad is adjacent the sample pad, the detection zone is adjacent the conjugate pad and the optional absorption pad is adjacent the detection zone.

The first element of the lateral flow test strip is the sample pad. Once soaked with sample—such as urine, the fluid migrates to the conjugate pad. This is where labeled specific binding agent(s) each capable of individually binding with the metabolites is present. Thus for example, labelled specific binding agent(s)—such as antibodies or fragments thereof, affimers or aptamers—each capable of individually binding to (i) cotinine and total NNAL; (ii) cotinine and CEMA; or (iii) cotinine and NNAL and CEMA will be present. The amounts thereof can be adjusted as required to fine-tune the sensitivity of the assay for each metabolite. Typically, the amount of each specific binding agent that is used will be different.

The detection zone will include at least two test lines which each contain a specific binding agent that is capable of individually capturing (i) cotinine and total NNAL labelled antibody complexes; or (ii) cotinine and CEMA labelled antibody complexes; or (iii) cotinine and NNAL and CEMA labelled antibody complexes. The exact configuration of the detection zone will depend upon the format of the assay—such as the sandwich or competitive format of the assay as discussed above. In one embodiment, the threshold at the detection zone is: (i) greater than or equal to about 200 ng/ml for 24 hour urinary cotinine and the threshold is greater than or equal to about 10 pg/ml for total NNAL in 24 hour urine or the threshold is greater than or equal to about 5 ng/ml for 24 hour urinary CEMA, and the detectable signal is generated when the threshold of detection is crossed; or (ii) the threshold is greater than or equal to about 200 ng/ml for 24 hour urinary cotinine and the threshold is greater than or equal to about 10 pg/ml for total NNAL in 24 hour urine and the threshold is greater than or equal to about 5 ng/ml for 24 hour urinary CEMA and a detectable signal is generated when the threshold of detection is crossed.

The portable lateral flow immunoassay device will typically comprise the lateral flow test strip contained in a housing—such as a liquid-tight or impervious housing—to allow the immersion of the device into a sample and to allow for only those necessary elements of the lateral flow test strip to be wetted. The device will normally have an elongated shape, the dimensions of which can vary, depending on the actual use of the device; exemplary dimensions are from 6 to 8 cm in length, and 3 to 6 mm in width.

One further example of a portable lateral flow immunoassay device is described in WO2007/023372, which discloses a device for determining a metabolite in a liquid sample, comprising a capillary diffusion means on which are materialised: a) a sample pad; b) an upstream release zone comprising a metabolite-specific detection reagent conjugated to a visible and/or measurable marker, which is free to migrate by capillary diffusion in a wet state in the capillary diffusion means; and c) at least two downstream conjugate pads comprising, successively in the capillary diffusion direction, on one hand, a metabolite-specific binding agent(s) and, on the other hand, the metabolite(s) or an analogue of the metabolite(s), which is immobilised. The reagent(s) allow for the determination of the metabolite(s) in the sample in a sandwich format.

Another example of a portable lateral flow immunoassay device that is contemplated for use herein is also described in WO02007/023372, which discloses a device for determining a metabolite in a liquid sample, comprising a capillary diffusion means on which are materialised: a) a sample pad; b) an upstream release zone comprising a metabolite-specific detection reagent conjugated to a visible and/or measurable marker, which is free to migrate by capillary diffusion in a wet state in the capillary diffusion means; and c) at least two downstream conjugate pads comprising, successively in the capillary diffusion direction, on one hand, a metabolite-specific binding agent(s) and, on the other hand, the metabolite(s) or an analogue of the metabolite(s), which is immobilised. The detection reagent(s) and metabolite(s), or the metabolite analogue(s), allow for the determination of the metabolite(s) of interest in the sample in a competition format. The detection reagent(s) can be deposited in excess at a detection zone which is formed upstream of the conjugate pads Another example of a portable lateral flow immunoassay device that is contemplated for use herein is one that is structured for the simultaneous determination of two or more (for example, several) metabolites as described in, for example, EP1657550. The device comprises a capillary diffusion means on which are materialised: a) a sample pad; b) an upstream conjugate pad comprising a mixture of detection reagents, each specific for one of the metabolites, conjugated to a visible and/or measurable marker, which are free to migrate by capillary diffusion in a wet state in the capillary diffusion means; and c) downstream conjugate pads each comprising a specific binding agent which is specific of one of the metabolites, said downstream conjugate pads being distributed successively according to the direction of migration.

Another example of a portable lateral flow immunoassay device that is contemplated for use herein is described in US2015/168397. A device for determining the presence and/or the amount of at least one (or two or more) metabolite capable of being contained in a liquid sample is disclosed, comprising a capillary diffusion means on which the liquid sample is intended to migrate laterally according to a direction and a way of capillary migration. The capillary diffusion means comprises a sample pad for depositing the sample, an upstream conjugate pad which comprises at least one (or two or more) detection reagent that is capable of moving as a consequence of the migration of the liquid sample in the capillary diffusion means, and at least two conjugate pads which can each comprise at least one (or two or more) specific binding agent immobilised on the capillary diffusion means. The device can further include at least one downstream detection zone which is formed on the capillary diffusion means and which is located downstream of at least one of the conjugate pads. The downstream detection zone can comprise at least one (two or more) detection reagent that is capable of moving as a consequence of the migration of the liquid sample in the capillary diffusion means. The detection reagent and/or the specific binding agent is then capable of specifically binding to the metabolite(s) and/or specifically binding to each other to form a complex allowing the determination of the metabolite(s) in the liquid sample at said complementary capture zone(s).

Figure 4:
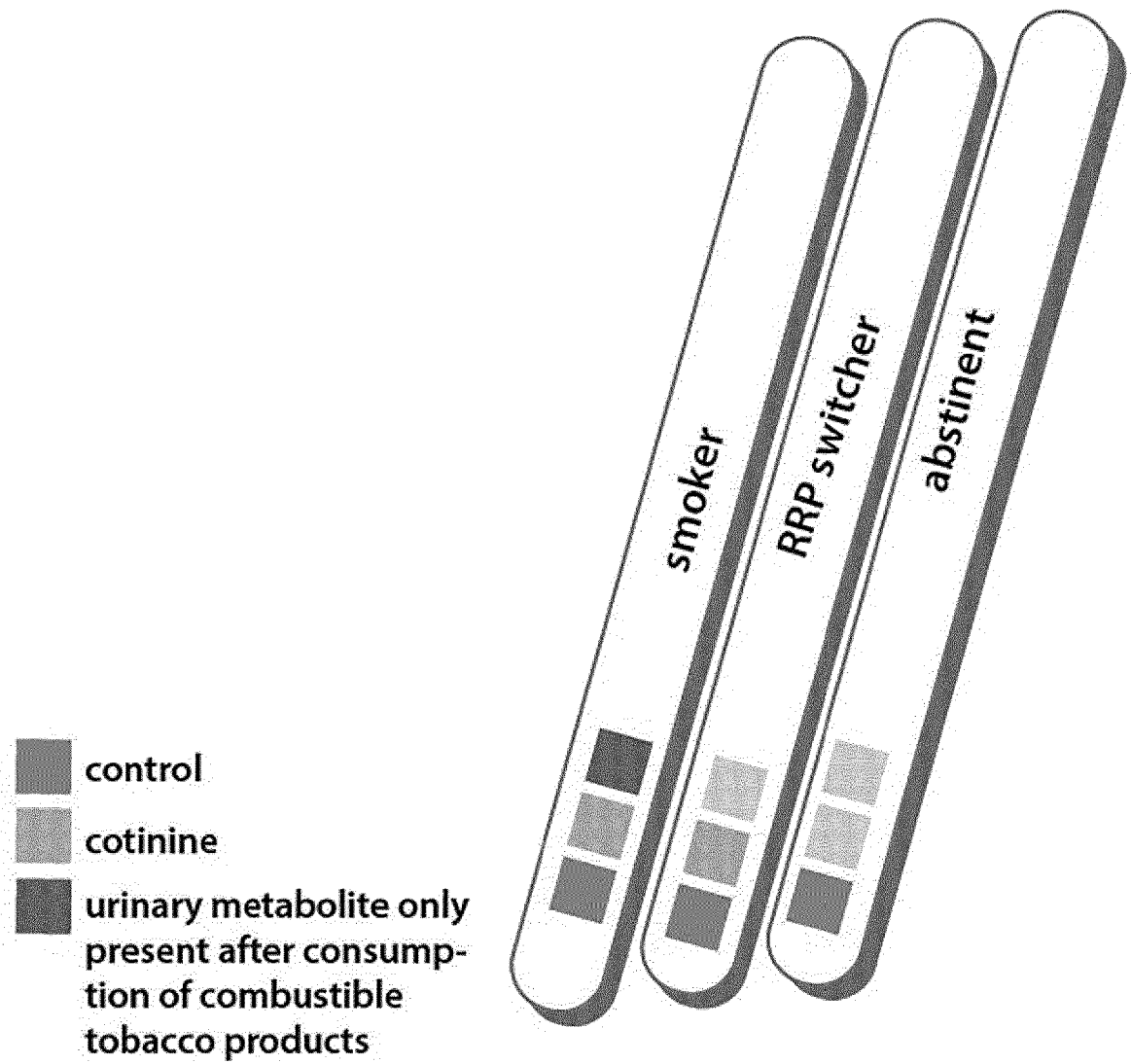
FIG. 4: An example of a dipstick containing a lateral flow test strip for determining the smoking status of a subject. In this exemplary embodiment, three different dipsticks are used, to determine the three different smoking statuses of the subject. In one embodiment, the dipstick is sensitive enough to detect urinary total NNAL in 24 hour-urine in an amount of 10-125 pg/ml and urinary CEMA in 24 hour urine in an amount of 5-80 ng/ml. In another embodiment, the dipstick is sensitive enough to detect urinary total NNAL in 24 hour-urine in an amount of 10-125 pg/ml and urinary CEMA in 24 hour urine in an amount of 5-80 ng/ml and urinary cotinine in an amount of about 200-800 ng/ml. Smoking status can be deduced using the dipstick.

Turning to FIG. 4 of the present application, there is described another example of a portable lateral flow immunoassay device in the form of a dipstick for determining or distinguishing the smoking status of a subject. Different smoking status results are shown.

In one embodiment, the dipstick is sensitive enough to detect urinary total NNAL in 24 hour urine in an amount of 10-125 pg/ml and urinary CEMA in 24 hour urine in an amount of 5-80 ng/ml. In another embodiment, the dipstick is sensitive enough to detect urinary total NNAL in 24 hour-urine in an amount of 10-125 pg/ml and urinary CEMA in 24 hour urine in an amount of 5-80 ng/ml and urinary cotinine in an amount of about 200-800 ng/ml. Smoking status can be deduced using the dipstick.

Figure 5:
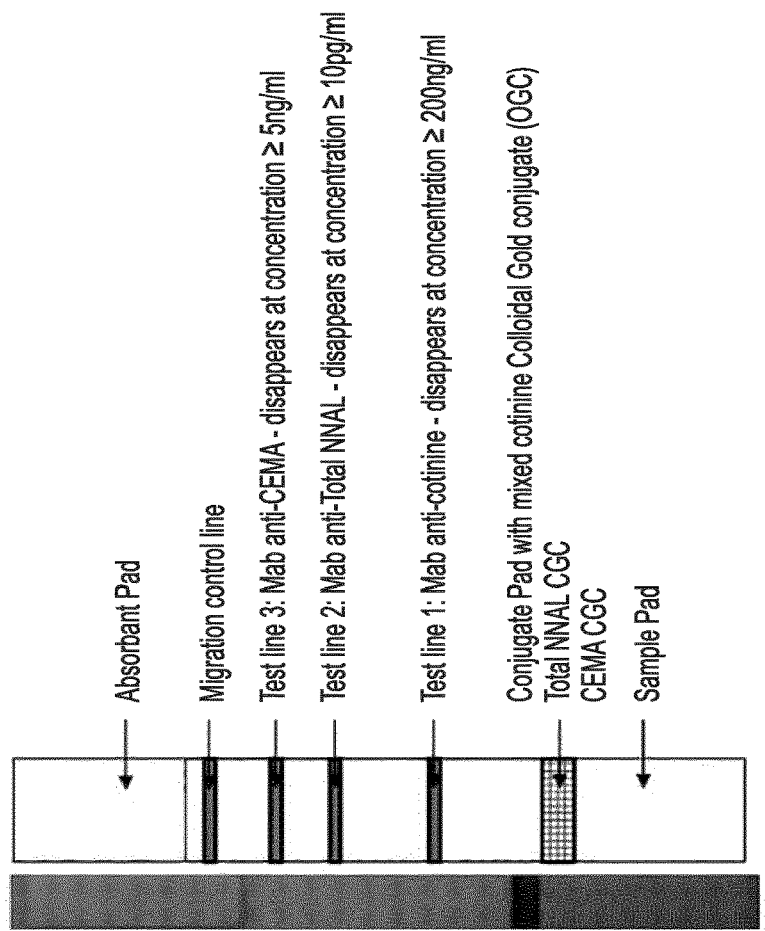
FIG. 5: An example of a dipstick containing a lateral flow test strip for determining the smoking status of a subject. In this exemplary embodiment, a single dipstick is used, to determine the three different smoking statuses of the subject. The single dipstick contains a porous element in the form of a sample pad and a porous element in the form of one or more absorption pads at opposing ends of the lateral flow test strip that is contained in the device. It further includes a porous element in the form of a conjugate pad adjacent and downstream (in the direction of flow of the sample) the sample porous element comprising cotinine colloidal gold conjugate (CGC), total NNAL CGC and CEMA CGC. Other kinds of label can be used, as required. Adjacent and downstream the conjugate porous element, three sequentially arranged test lines are included in a detection zone. One first test line 1 can contain anti-cotinine monoclonal antibody or a fragment thereof. This test line can be configured to indicate that a threshold of detection has been crossed (for example, disappears or appears depending on the assay format) at a threshold amount of greater than or equal to about 200 ng/ml. One following second test line 2 can contain anti-total NNAL monoclonal antibody or a fragment thereof. This test line can be configured to indicate that a threshold of detection has been crossed (for example, disappears or appears depending on the assay format) at a threshold amount of greater than or equal to about 10 pg/ml. One third test line 3 can contain anti-CEMA monoclonal antibody or a fragment thereof. This test line can be configured to indicate that a threshold of detection has been crossed (for example, disappears or appears depending on the assay format) at a threshold amount of greater than or equal to about 5 ng/ml. A control line can also be included, as required. Other kinds of specific binding agents can be used, as required.
Figure 5:
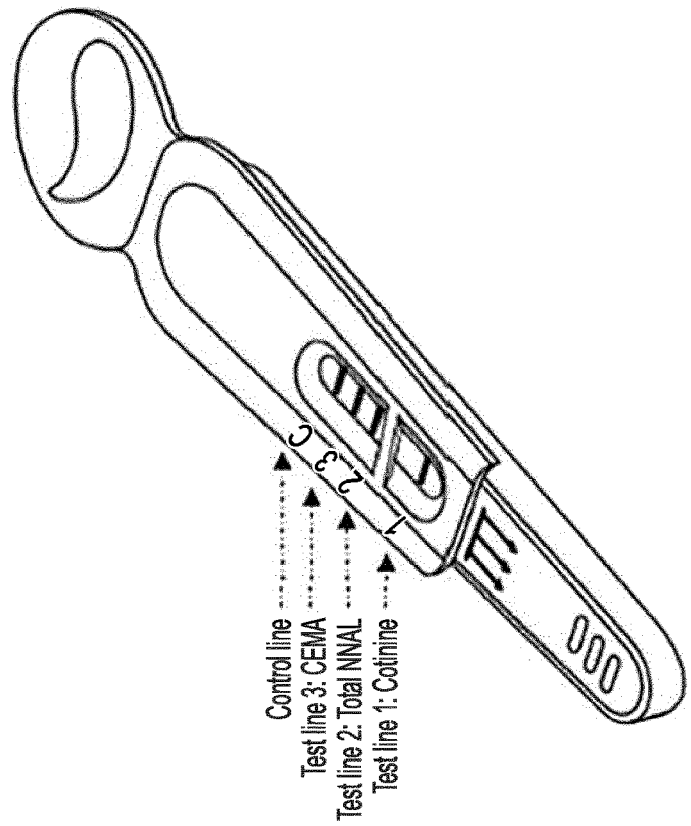

FIG. 5 illustrates another example of a portable lateral flow immunoassay device in the form of a dipstick for determining the smoking status of a subject. In this example, a dipstick is used to distinguish three possible different smoking statuses of the subject. The dipstick contains a sample pad and an optional absorption pad at opposing ends of the lateral flow test strip that is contained in the device. It further includes a conjugate pad adjacent the sample pad containing three different specific binding agents—such as a cotinine colloidal gold labelled specific binding agent, a total NNAL colloidal gold labelled specific binding agent and a CEMA labelled specific binding agent. Each of the three different specific binding agents can be present at their desired concentrations. For each metabolite, the concentrations of the specific binding agents can each be adjusted to fine-tune the sensitivity of the assay for that metabolite (for example, change the detection threshold), which is routine experimentation for the ordinary skilled person.

Adjacent the conjugate pad, a detection zone is present comprising three sequentially arranged test lines. An optional control test line can be included. The dipstick is configured for use in the competitive format. One test line can contain means to detect cotinine—such as an anti-cotinine monoclonal antibody or a fragment thereof. This test line can be configured to disappear at a threshold amount of greater than or equal to about 200 ng/ml.

Figure 6:
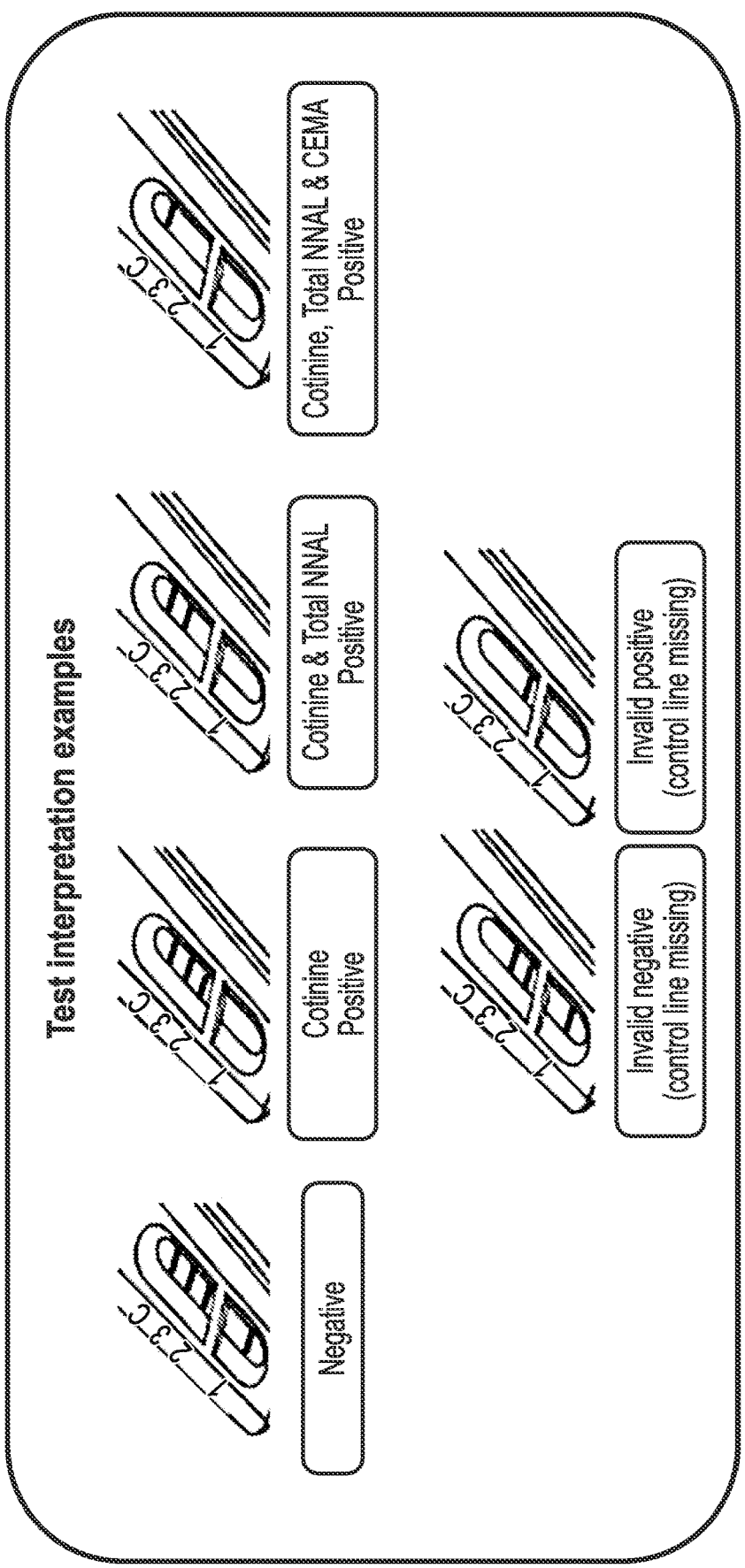
FIG. 6: An example of test interpretation results that can be obtained using the dipstick of FIG. 5 in a competitive format. Exemplary interpretation examples that can be related to a subject's smoking status is as follows: Box labelled 'Negative'=visible indications at cotinine test lines, NNAL test lines, CEMA test lines indicates that the threshold of detection has not been passed and is indicative of a non-smoking subject; Box labelled "Cotinine Positive"=no visible indication of cotinine indicates that the threshold of detection has been passed; visible indication at NNAL line, visible indication at CEMA line indicates that the threshold of detection has not been passed and is indicative of subject only exposed to heated tobacco (aerosol); Box labelled Cotinine and total NNAL positive and/or Cotinine, total NNAL and CEMA positive'=no visible indications at cotinine and total NNAL indicates that the threshold of detection has been passed or no visible indications at cotinine and total NNAL and CEMA indicates that the threshold of detection has been passed and is indicative of a subject exposed to combusted tobacco.

One test line can contain means to detect total NNAL—such as anti-total NNAL monoclonal antibody or a fragment thereof. This test line can be configured to disappear at a threshold amount of greater than or equal to about 10 pg/ml. One test line can contain means to detect CEMA—such as anti-CEMA monoclonal antibody or a fragment thereof. This test line can be configured to disappear at a threshold amount of greater than or equal to about 5 ng/ml. An example of the test interpretation results that can be obtained using the kind of dipstick can be seen in FIG. 6.

In one embodiment, the device is a competition format test device for the qualitative determination of tobacco smoke exposure biomarkers. Such an example can be seen in FIG. 5. The device comprises a lateral flow test strip housed in a liquid-tight or impervious housing allowing the immersion of the device into a sample. The housing can comprise or consist of plastic. The sample can be a liquid sample—such as urine. The lateral flow test strip can be made of different superimposed porous elements which are assembled together on a support—such as a plastic or PVC support to confer rigidity to the strip. The strip can have an elongated shape, the dimensions of which can vary, depending on the actual use of the device; exemplary dimensions are from 6 to 8 cm in length, and 3 to 6 mm in width. The sample pad can be made of various absorbent materials—such as cellulose paper material.

The conjugate pad can be made of various materials—such as glass fiber. Other pads forming part of the lateral flow test strip can be made of nitrocellulose. If required, before assembling the pads, one or more of them can be chemically and/or biochemically treated, or modified, to obtain sample permeability, and/or sample capillary migration. Transfer or flow can occur throughout and along the whole lateral flow test strip. If necessary, similar treatments can be performed before or after bringing the reagent(s) onto the pads, for example, to obtain the required immunochemical interaction(s) with the strip, in particular in the test line(s) of the detection zone. Exemplary detection agents are coloured particles—such as colloidal gold. Such particles are available in different sizes (typically from about 40 to about 100 nanometers), and in different colours. The different conjugates with colored particles (for example, colloidal gold) with one or more, or two or more, or three or more of cotinine, total NNAL, and CEMA, can be mixed together in liquid phase, deposited, and dried on the conjugate pad. Three specific anti-cotinine, anti-total NNAL, and anti-CEMA specific binding agents—such as monoclonal antibodies—can be deposited and immobilised on the nitrocellulose membrane of the lateral flow test strip in or along three different transverse test lines in the detection zone. An appropriate specific reagent can be also deposited on the test device to form a control line at the downstream end of the strip in the detection zone. An anti-THP or anti-creatinine specific binding agent—such as a monoclonal antibody—or a fragment thereof matched pair can be used on the lateral flow test strip to obtain a urine positive control line, also at the downstream end of the strip in the detection zone.

A kit for determining the smoking status of a subject is also disclosed comprising: a portable lateral flow immunoassay device—such as a dipstick having at least two different conjugate pads arranged on the dipstick and, deposited on each conjugate pad, a different specific binding agent moiety, each specific binding agent capable of capturing a different one of the metabolites described herein. Optionally, a set of instructions for determining the smoking status of the subject can be included in the kit.

A portable lateral flow immunoassay device—such as a dipstick—for determining the smoking status of a subject is also disclosed comprising at least two different conjugate pads arranged on the device and, deposited on each conjugate pad, a different specific binding agent, each specific binding agent being capable of individually binding to a different one of the metabolites described herein.

The use of the kit or the device for determining the smoking status of a subject is also disclosed.

Portable Device for Home, Clinical or Laboratory Use

Also disclosed herein are portable devices, such as, for example, devices, for use at home or in clinical or laboratory settings and kits comprising same for determining the smoking status of a subject.

A related aspect thus provides a portable testing device capable of measuring the presence and/or quantity of the metabolites as taught herein in a sample from a subject comprising: (i) means for obtaining a sample from the subject, (ii) means for measuring the quantity of the metabolites in said sample, and (iii) means for visualising the quantity of said metabolites in the sample.

In an embodiment, said visualising means is capable of indicating whether the quantity of the metabolites in the subject deviates from (for example, is below or above) a certain reference or base-line value. Hence, the portable testing device may suitably also comprise said reference or base-line value or means for establishing the same.

A relative quantity of a molecule or analyte in a sample can be expressed as an increase or decrease or as a fold-increase or fold-decrease relative to said another value, such as relative to a reference value. Performing a relative comparison between first and second variables (e.g., first and second quantities) may but need not require to first determine the absolute values of said first and second variables. For example, a measurement method may produce quantifiable readouts (such as, e.g., signal intensities) for said first and second variables, wherein said readouts are a function of the value of said variables, and wherein said readouts can be directly compared to produce a relative value for the first variable vs. the second variable, without the actual need to first convert the readouts to absolute values of the respective variables.

Any of the metabolites may be measured collectively, such that the measured quantity corresponds to the sum amounts of the collectively measured species. In another example, any metabolite may be measured each individually.

Mass Spectrometric Techniques

This technique can also be used to detect one or more of the metabolites described herein. Generally, any mass spectrometric (MS) techniques that can obtain precise information on the mass of molecules are useful herein. Suitable MS and MS/MS techniques and systems are well-known per se (see, e.g., LC/MS: A Practical User's Guide by Marvin C. McMaster ISBN: 9780471655312; Methods in Molecular Biology, vol. 146: "Mass Spectrometry of Proteins and Peptides", by Chapman, ed., Humana Press 2000, ISBN 089603609x; Biemann 1990. Methods Enzymol 193: 455-

79; or Methods in Enzymology, vol. 402: "Biological Mass Spectrometry", by Burlingame, ed., Academic Press 2005, ISBN 9780121828073) and may be used herein. MS arrangements, instruments and systems suitable for the analysis of chemical or biological species may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI- (MS)$^n$; atmospheric pressure photoionization mass spectrometry (APPI-MS); APPI-MS/MS; and APPI- (MS)$^n$. Detection and quantification of chemical species by mass spectrometry may involve multiple reaction monitoring (MRM), such as described among others by Roepstorff & Fohlman (Biomed. Mass Spectrom. (1984) 11, 601). MS analysis methods may be advantageously combined with upstream chemical species separation or fractionation methods, such as for example with the chromatographic and other methods described herein below.

Chromatography

Chromatography may also be used for measuring chemical species including the metabolites described herein. The term "chromatography" encompasses methods for separating chemical substances, referred to as such and vastly available in the art. In a preferred approach, chromatography refers to a process in which a mixture of chemical substances carried by a moving stream of liquid or gas ("mobile phase") is separated into components as a result of differential distribution of the metabolites, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like.

Chromatography as used herein may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilised metal affinity chromatography, and the like.

Kits

The disclosure further provides kits for the detection of the metabolites as taught herein comprising means for detecting the level of one or more metabolite(s) as taught herein in a sample from a subject. In a preferred embodiment, such a kit or kits are ideally designed for use at home or by a doctor in a general practice setting.

Further disclosed is a kit, particularly a kit for determining the smoking status of a subject as taught herein in a subject, the kit comprising (i) means for measuring the metabolites as taught herein, particularly in a sample from the subject, and (ii) optionally a reference value for the metabolite or metabolites or means for establishing said reference value, wherein said reference value represents detection of the metabolites.

A home-test kit may give the subject a readout which he/she can communicate to a medicinal practitioner, after which appropriate action can be taken. Non-limiting examples are: systems comprising specific binding molecules for the requisite metabolites(s) attached to a solid phase, e.g. a portable lateral flow immunoassay device—such as a dipstick. One non-limiting example is to use a lateral flow test-strip and labelled specific binding agent (for example, in a sandwich format) which combination does not require any washing of a membrane. The lateral flow test strip is well known, for example, in the field of pregnancy testing kits where a first anti-hCG antibody is present on the support, and is carried complexed with hCG by the flow of urine onto an immobilised second anti-hCG antibody that permits visualisation. Other non-limiting examples of such home test devices, systems or kits may be found for example in the following U.S. Pat. Nos. 6,107,045, 6,974,706, 5,108,889, 6,027,944, 6,482,156, 6,511,814, 5,824,268, 5,726,010, 6,001,658 or U.S. patent applications: 2008/0090305 or 2003/0109067.

The means for measuring the presence and/or quantity of the metabolites in the kits may comprise one or more specific binding agents capable of specifically binding to said metabolite(s). The one or more specific binding agents may be inter alia an antibody or a fragment thereof, aptamer, affimer, photoaptamer, protein, peptide, peptidomimetic or a small molecule. The kits of the disclosure may comprise one or more aptamers, affimers, or antibodies or fragments thereof, more preferably one or more antibodies or fragments thereof capable of specifically binding to said one or more metabolites as taught herein. A binding agent may be advantageously deposited or immobilised on a solid phase or support.

The kits may employ an immunoassay technology or mass spectrometry analysis technology or chromatography technology, or a combination of said technologies. Suitably, the kits employ an immunoassay technology, in preferred but non-limiting examples, enzyme-linked immunosorbent assay (ELISA), radioimmunoassay (RIA), fluorescent immunoassay, chemiluminescent immunoassay, DRI immunoassay, quantitative immunoassy, lateral flow immunoassay, microfluidic immunoassay and agglutination immunoassay technologies, preferably using ELISA. Alternatively, or in addition, the presence and/or quantity of any one or more metabolites as taught herein may be measured using techniques that are antibody- or chromatography-based, using competitive format or sandwich format binding assays and/or using derivatising and/or colourant-bearing agents. Hence, the means for measuring the quantity of marker(s) may be an immunoassay, e.g., an immunoassay employing antibody(ies) or fragments thereof or aptamers or affimers either separately or in combination, e.g., ELISA or RIA assay.

Accordingly, there is disclosed a kit, particularly a kit for the detection of the metabolites as taught herein in a subject, the kit comprising: (i) one or more specific binding agents capable of specifically binding to the metabolites described herein, particularly in a sample from the subject, (ii) preferably, a known quantity or concentration of said metabolites (e.g., for use as controls, standards and/or calibrators), (iii) optionally and preferably a reference value for the metabolite or metabolites or means for establishing said reference value, wherein said reference value represents detection of the metabolites. Said components under (i) and/or (ii) may be suitably labelled as described herein.

There is also disclosed a kit for determining the smoking status of a subject comprising or consisting of: (i) a first device adapted to detect the presence of a tobacco smoke exposure biomarker in a biological sample, wherein said biomarker consists of cotinine; (ii) a second device adapted to detect the presence of a tobacco smoke exposure biomarker in a biological sample, wherein said biomarker consists of NNAL; and/or (iii) a third device adapted to detect the presence of a tobacco smoke exposure biomarker in a biological sample, wherein said biomarker consists of CEMA; and optionally, a set of instructions for determining the smoking status of the subject. Each device will typically comprise specific binding molecules for cotinine or total NNAL or CEMA attached to a solid phase, suitably, wherein the device is a portable lateral flow immunoassay device—such as a dipstick.

Typically, the specific binding molecules of the first device are adapted to detect urinary cotinine in an amount of about 200-800 ng/ml. Typically, the specific binding molecules of the second device are adapted to detect urinary total NNAL in 24 hour-urine in an amount of 10-125 pg/ml. Typically, the specific binding molecules of the third device are adapted to detect urinary CEMA in 24 hour urine in an amount of 5-80 ng/ml. The amounts of the metabolites can be measured using immunoassay, suitably, enzyme-linked immunosorbent assay (ELISA), radioimmunoassay (RIA), fluorescent immunoassay, chemiluminescent immunoassay, DRI immunoassay, quantitative immunoassy, lateral flow immunoassay, microfluidic immunoassay, agglutination immunoassay, ELISA, or antibody- or chromatography, suitably, competitive binding assays or assays utilising derivatising and/or colourant-bearing agents. The specific binding molecules can be selected from the group consisting of an antibody or a fragment thereof, an aptamer, a photoaptamer, a protein, a peptide, a peptidomimetic or a small molecule or a combination of two or more thereof.

Each device can be an immunochromatographic device, suitably, a lateral flow immunochromatographic device. Further disclosed is the use of a kit as described herein for the detection of the metabolites taught herein.

Also disclosed is a binding agent array or microarray comprising one or more binding agents capable of specifically binding to the metabolites as taught herein, preferably a known quantity of, or concentration of said binding agents. Such binding agents may be as detailed herein.

Labels

In some embodiments, reagents disclosed herein may comprise a detectable label. The term "label" refers to any atom, molecule, moiety or biomolecule that can be used to provide a detectable and preferably quantifiable read-out or property, and that may be attached to or made part of an entity of interest, such as a metabolite or a specific-binding agent. Labels may be suitably detectable by mass spectrometric, spectroscopic, optical, colourimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish phosphatise or alkaline phosphatise as commonly used in immunoassays); binding moieties such as biotin-streptavidin; haptens such as digoxigenin; luminogenic, phosphorescent or fluorogenic moieties; mass tags; and fluorescent dyes alone or in combination with moieties that can suppress or shift emission spectra by fluorescence resonance energy transfer (FRET). Other kinds of labels are also described herein—such as coloured particles, for example gold nanoparticles.

For example, the label may be a mass-altering label. Preferably, a mass-altering label may involve the presence of a distinct stable isotope in one or more chemical moiety of the metabolite vis-à-vis its corresponding non-labelled metabolite. Mass-labelled moieties are particularly useful as positive controls, standards and calibrators in mass spectrometry applications. In particular, molecules including one or more distinct isotopes are chemically alike, separate chromatographically and electrophoretically in the same manner and also ionise and fragment in the same way. However, in a suitable mass analyser such molecules will display distinguishable m/z ratios and may thus be discriminated. Examples of pairs of distinguishable stable isotopes include H and D, $^{12}C$ and $^{13}C$, $^{14}N$ and $^{15}N$ or $^{16}O$ and $^{18}O$.

Also contemplated is the use of metabolites as taught herein, optionally comprising a detectable label, as (positive) controls, standards or calibrators in qualitative or quantitative detection assays (measurement methods) of said metabolites, and particularly in such methods for the detection of the metabolites as taught herein in subjects. The metabolites may be supplied in any form, inter alia as precipitate, in solution as liquid or frozen, or covalently or non-covalently immobilised on solid phase, such as for example, on solid chromatographic matrix or on glass or plastic or other suitable surfaces (e.g., as a part of an array or microarrays).

Deviation

A "deviation" of a first value from a second value may generally encompass any direction (e.g., increase: first value >second value; or decrease: first value <second value) and any extent of alteration. For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD, or ±1×SE or ±2×SE). Deviation may also refer to a value falling outside of a reference range defined by values in a given population (for example, outside of a range which comprises ≥40%, ≥50%, ≥60%, >70%, ≥75% or ≥80% or ≥85% or ≥90% or ≥95% or even ≥100% of values in said population).

A deviation may be concluded if an observed alteration is beyond a given threshold or cut-off. Such threshold or cut-off may be selected as generally known in the art to provide for a chosen sensitivity and/or specificity of the detection methods, e.g., sensitivity and/or specificity of at least 50%, or at least 60%, or at least 70%, or at least 80%, or at least 85%, or at least 90%, or at least 95%.

Further Methods

The presence and/or concentration of metabolites(s) in a sample may be measured by surface plasmon resonance (SPR) using a chip having binding molecule for said metabolite(s) immobilised thereon, fluorescence resonance energy transfer (FRET), bioluminescence resonance energy transfer (BRET), fluorescence quenching, fluorescence polarisation measurement or other means known in the art. Any of the binding assays described may be used to determine the presence and/or concentration of any metabolite(s) in a sample. To do so, binding molecules for the metabolite(s) are reacted with a sample, and the concentration of the metabolite(s) is measured as appropriate for the binding assay being used. To validate and calibrate an assay, control reactions using different concentrations of standard metabolite(s) and/or binding molecule therefore may be performed. Where solid phase assays are employed, after incubation, a washing step is performed to remove unbound metabolites. Bound metabolite is measured as appropriate for the given label (e.g., scintillation counting, fluorescence, antibody-dye etc.). If a qualitative result is desired, controls and different concentrations may not be necessary. Of course, the roles of said metabolite(s) and binding molecule may be switched; the skilled person may adapt the method so binding molecule is applied to sample, at various concentrations of sample.

Further chemical species separation, identification or quantification methods may be used, optionally in conjunction with any of the above described analysis methods, for measuring metabolites in the present disclosure. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

Stereo and Geometric Isomers

The metabolites disclosed herein may exist as stereoisomers and/or geometric isomers. They may possess one or more asymmetric and/or geometric centres and so may exist in two or more stereoisomeric and/or geometric forms. The disclosure contemplates the use of all of the individual stereoisomers and geometric isomers thereof, and mixtures thereof.

Reducing Smoking of Conventional Cigarettes

If it is deduced that the subject that has been tested is a consumer of conventional cigarettes then the subject may be administered one or more therapies to reduce smoking of conventional cigarettes based upon this test result.

Many therapies have been developed for aiding smokers to reduce smoking of conventional cigarettes, the predominate one being nicotine replacement therapies. Nicotine replacement therapies involve the administration of nicotine through a suitable delivery system. Nicotine replacement products that are currently on the market includes (1) nicotine transdermal patches, such as NicoDerm® CQ) (GlaxoSmithKline), Habitro® (Novartis Consumer Health), and Nicotrol® (Pharmacia Consumer Healthcare); (2) nicotine gum, such as Nicorette® (GlaxoSmithKline); (3) nicotine nasal spray, such as Nicotrol NS® (Pharmacia Consumer Healthcare); and (4) nicotine inhaler (Nicotrol® nicotine inhalation system (Pharmacia Consumer Healthcare). Antidepressants have also been developed or proposed as therapy for smoking cessation. One of such antidepressants is bupropion. Other antidepressants proposed for smoking cessation treatment include doxepin, imipramine. Anxiolytics have also been explored or proposed as therapy for smoking cessation, which include, for example, isovaleramide, diazepam, meprobamate, metoprolol, ondansetron, and oxprenolol. Another class of agents that has been explored as therapy for smoking cessation is nicotine receptor antagonists, examples of which include mecamylamine, hexamethonium, dihydro-beta-erythroidine and d-tubocurarine. Still another class of agents is opioid antagonists—such as naltrexone (also know as 17-(cyclopropylmethyl)-4,5-epoxy-3,14-dihydroxymo hinan-6-one), naloxone (also known as 4,5-epoxy-3,14-dihydroxy-17-(2-prophenyl)morphinan-6-one), and nalmefene (also known as 5alpha-17-(cyclopropylmethyl)-4,5-epoxy-6-methylenemorphinan-3,14-diol).

Insurance

The present disclosure can find application in determining suitability for insurance or in calculating insurance premiums based upon the subject's smoking status. Thus, in a further aspect there is provided a method for determining suitability for insurance or in calculating insurance premiums based upon a subject's smoking status comprising: (i) measuring in a biological sample from the subject the amounts of two or three metabolites in the sample, said metabolites consisting of cotinine and one or more of total NNAL and CEMA: (ii) based on the measurements in (i) determining the smoking status of the subject; and (iii) based on the determination of smoking status in (ii) determining the subject's suitability for insurance or calculating an insurance premium based upon the subject's smoking status.

Clinical Trials

The present disclosure can find application in clinical trials. By way of example, if compliance with a clinical trial requires that a subject has a particular smoking status then the present disclosure can be used to monitor or check this smoking status. Thus, in a further aspect there is provided a method for determining a subject's compliance with a clinical trial comprising: (i) measuring in a biological sample from the subject the amounts of two or three metabolites in the sample, said metabolites consisting of cotinine and one or more of total NNAL and CEMA: (ii) based on the measurements in (i) determining the smoking status of the subject; and (iii) based on the determination of smoking status in (ii) determining the subject's compliance with the clinical trial.

If it is determined that the subject has not complied with the requirements of the clinical trial then the subject may be removed from the clinical trial.

If it is determined that the subject has not complied with the requirements of the clinical trial then the data originating from that subject may be removed from the clinical trial.

In related aspect, it may be determined that a subject has not complied with the smoking status of the clinical trial in which case the non-compliant subject may be removed from the trial or the data from the non-compliant subject may be removed from the clinical trial.

Computing

A system is also described herein comprising: a computer data repository that comprises or consists of a reference value of the quantity of cotinine and one or more of total NNAL and CEMA, said reference value representing a known quantity of metabolite for determining the smoking status of a subject; and a computer system programmed to access the data repository and to use information from the data repository in combination with information on the quantity of metabolites in the sample from a subject, to make a determination of the smoking status of the subject. A method for determining the smoking status of a subject comprising the use of the system and the use of the system for determining smoking status is also disclosed. The techniques and devices may be implemented on any suitable hardware, including a programmed computing system. The disclosure is operational with numerous general purpose or special purpose computing system environments or configurations. Examples of well-known computing systems, environments, and/or configurations that may be suitable for use can include, but are not limited to, personal computers, server computers, hand-held or laptop devices, multiprocessor systems, microprocessor-based systems, set top boxes, programmable consumer electronics, network PCs, minicomputers, mainframe computers, distributed computing environments or cloud-based computing environments that include any of the above systems or devices, and the like. The computing environment may execute computer-executable instructions, such as program modules. Generally, program modules include routines, programs, objects, components, data structures, etc. that perform particular tasks or implement particular abstract data types. The disclosure may also be practiced in distributed computing environments where tasks are performed by remote processing devices that are linked through a communications network. In a distributed computing environment, program modules may be located in both local and remote computer storage media including memory storage devices. Components of a system for use in the present disclosure may include, but are not limited to, a processing unit, a system memory, and a system bus that couples various system components including the system memory to the processing unit. The system bus may be any of several types of bus structures including a memory bus or memory controller, a peripheral bus, and a local bus using any of a variety of bus architectures. By way of example and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The computer typically includes a variety of computer readable media, which are well known in the art.

As required, the test can be associated to a mobile reader that allows the automatic communication of the test results, optionally in real time.

Further aspects of the present disclosure are set forth below in the following numbered paragraphs:

1. A method for determining the smoking status of a subject comprising: (i) measuring in a biological sample from the subject the amounts of two or three metabolites in the sample, said metabolites consisting of cotinine and one or more of total NNAL and CEMA: and (ii) based on the measurements in (i) determining the smoking status of the subject.

2. A method for determining the smoking status of a subject, comprising: (i) measuring the quantity of two or three metabolites in a sample from the subject, said metabolites consisting of cotinine and one or more of total NNAL and CEMA; (ii) comparing the quantity of the metabolites as measured in step (i) with a reference or baseline value representing a known amount of cotinine and total NNAL and/or CEMA; (iii) finding a deviation or no deviation of the amount of cotinine and total NNAL and/or CEMA as measured in (i) from the reference or baseline value; and (iv) attributing said finding of deviation or no deviation to the smoking status of the subject.

3. A method of monitoring the progression of a subject's change in smoking status comprising: (i) performing the method according to paragraph 1 or paragraph 2 on at least two biological samples from the subject, wherein each sample is taken at different time points; and (ii) comparing the measurements taken for each of the different time points, wherein a change in the measurements over time is indicative that the subject's smoking status has changed over time.

4. A method for determining the smoking status of a subject comprising: (i) receiving data representative of values of the quantity of two or three metabolites in a sample from a subject, said metabolites consisting of cotinine and one or more of total NNAL and CEMA; (ii) accessing a data repository on a computer, said data repository comprising a reference or baseline value for the quantities of cotinine and total NNAL and/or CEMA that are diagnostic for determining the smoking status of a subject; and (iii) comparing the data as received in (i) with the reference or baseline value in the data repository on the computer recited in (ii), thereby determining the smoking status in the subject.

5. A method of distinguishing the smoking status of a subject, said method comprising: (i) obtaining or providing a sample from a subject; (ii) detecting the amounts of two or three metabolites in the sample, wherein said metabolites consist of cotinine and total NNAL and/or CEMA, by contacting the sample with anti-cotinine and anti-total NNAL and/or anti-CEMA antibody and detecting binding between cotinine and total NNAL and/or CEMA and the antibodies; and (iii) determining the smoking status of the subject based on detecting the presence of cotinine and total NNAL and/or CEMA in the sample.

6. A method of determining the smoking status of a subject and administering one or more therapies to reduce smoking of conventional cigarettes, said method comprising: (i) obtaining or providing a sample from a subject; (ii) detecting whether two or three metabolites are present in the sample, said metabolites consisting of cotinine and total NNAL and/or CEMA; (iii) determining the smoking status of the subject; and (iv) depending on the result obtained in (iii) administering an effective amount of one or more therapies to reduce smoking of conventional cigarettes.

7. A method of diagnosing and reducing the smoking of conventional cigarettes in a subject, said method comprising: (i) obtaining a sample from a subject; (ii) detecting whether cotinine and one or more of total NNAL and CEMA is present in the sample; and (iii) in a subject diagnosed as a smoker, administering an effective amount of one or more therapies to reduce the smoking of conventional cigarettes in the subject.

8. The method of any of the preceding paragraphs, wherein the biological sample is urine, suitably, 24-hour urine.

9. The method of any of the preceding paragraphs, wherein the amounts of the metabolites are measured based upon the amount of signal generated.

10. The method of any of the preceding paragraphs, wherein the amounts of the metabolites are measured using immunoassay, suitably, enzyme-linked immunosorbent assay (ELISA), radioimmunoassay (RIA), fluorescent immunoassay, chemiluminescent immunoassay, DRI immunoassay, quantitative immunoassy, lateral flow immunoassay, microfluidic immunoassay, agglutination immunoassay, ELISA, or antibody- or chromatography, suitably, competitive binding assays or assays utilising derivatising and/or colourant-bearing agents.

11. The method according to any of the preceding paragraphs, wherein the amounts of metabolites are measured after 2 and/or 5 days of the investigational period in 24 hour urine, suitably, wherein the amounts of metabolites are compared against a baseline value for each of the metabolites.

12. A device for determining the smoking status of a subject, wherein said device is adapted to detect the presence of two or three metabolites in a biological sample, said metabolites consisting of cotinine and total NNAL and/or CEMA.

13. The device according to paragraph 12, comprising specific binding molecules for cotinine and total NNAL and/or CEMA attached to a solid phase, suitably, wherein the device is a lateral flow strip or a dipstick device.

14. A system comprising: (i) a computer data repository that comprises or consists of a reference or baseline value of the quantity of cotinine and one or more of total NNAL and CEMA, said reference or baseline values representing a known quantity of metabolite for determining the smoking status of a subject; and (ii) a computer system programmed to access the data repository and to use information from the data repository in combination with information on the quantity of metabolites in the sample from a subject, to make a determination of the smoking status of the subject.

The invention is further described in the Example below, which is provided to describe the invention in further detail. This example, which sets forth a preferred mode presently contemplated for carrying out the invention, is intended to illustrate and not to limit the invention.

EXAMPLE

This example is a randomized, controlled, open-label, 3-arm parallel group, multi-center study to demonstrate reductions in exposure to selected smoke constituents in conventional cigarettes (CC). The study included healthy smokers switching to a heat-not-burn (smoke-free alternative (SW)) product or those observing smoking abstinence (SA), compared with continuing to use CC, for 5 days in confinement and prolonged by 85 days in an ambulatory setting. This was an ad libitum smoking study. Baseline measurements are taken by allowing the subject to smoke their chosen brand of conventional cigarette for 2 days. After this 2 day period, the subject is then elected to continue smoking conventional cigarettes, to switch to a smoke-free alternative or to abstain from smoking. The investigational period then begins. Methods for measuring each of the metabolites are described in Haziza et al. (2017) *Data in Brief* 10, 283-293.

During the confinement period, compliance to product/regimen allocation (exclusive use of smoke-free alternative and CC in SW and CC arms, respectively, and full abstinence from smoking in the SA arm) was ensured by strict distribution of each tobacco stick/CC when requested by the subject. During the ambulatory period, the subjects randomized to the SW arm were instructed to exclusively use HNB products and subjects randomized to the SA arm were instructed to abstain from smoking.

The total NNAL (pg/ml), CEMA (ng/ml) and free cotinine (ng/ml) were measured in urine and the interquartile range (IQR=[$1^{st}$ quartile; $3^{rd}$ quartile]) is reported in the table below. Furthermore, the data are represented as boxplots in the figures below. The bottom of the box is the first quartile (value below which 25% of the observations lie), the top is the third quartile (value below which 75% of the observations lie) and the middle bar is the median of the observations. The whiskers extend to the minimum observed value and maximum observe value respectively.

As can be seen in FIGS. 1-3 and in Table 1, CEMA and Cotinine can achieve a separation of CC and SA subject after 2 days with a specificity and sensitivity of at least 75%, while Total NNAL is providing the same levels of discrimination between day 5 and day 30. The subjects in the SW arm can be distinguished from the CC arm based on the CEMA and Total NNAL after day 5 with a specificity and sensitivity of at least 75%. Finally, subjects in the SW arm can be distinguished from the subjects in the SA arm based on the Free Cotinine after 2 days (with a specificity and sensitivity of at least 75%).

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 1

Interquartile ranges for the CEMA, Cotinine and Total NNAL in each arm for every sampling time point (IQR = [$1^{st}$ quartile; $3^{rd}$ quartile])

| Biomarker/Arm | CEMA (ng/mL) CC | CEMA (ng/mL) SA | CEMA (ng/mL) SW | Free Cotinine (mg/mL) CC | Free Cotinine (ng/mL) SA |
|---|---|---|---|---|---|
| Baseline | [39.20; 99.50] | [39.90; 83.50] | [35.70; 74.25] | [546.0; 1280.0] | [576.0; 1190.0] |
| Day −1 | [48.80; 119.00] | [48.10; 108.00] | [42.90; 96.99] | [574.0; 1430.0] | [608.0; 1430.0] |
| Day 0 | [39.20; 99.50] | [39.90; 83.50] | [35.70; 74.25] | [545.0; 1260.0] | [576.0; 1190.0] |
| Day 1 | [46.40; 103.00] | [18.40; 48.70] | [15.85; 41.05] | [559.0; 1480.0] | [339.0; 959.0] |

TABLE 1-continued

Interquartile ranges for the CEMA, Cotinine and Total NNAL in each arm for every sampling time point (IQR = [$1^{st}$ quartile; $3^{rd}$ quartile])

| | | | | | |
|---|---|---|---|---|---|
| Day 2 | [32.60; 98.30] | [7.83; 17.30] | [8.49; 17.90] | [459.0; 1350.0] | [128.00; 313.00] |
| Day 3 | [28.40; 82.90] | [5.70; 14.60] | [7.50; 15.25] | [481.0; 1250.0] | [60.30; 156.00] |
| Day 4 | [42.50; 106.00] | [5.34; 15.80] | [6.85; 16.60] | [392.0; 1370.0] | [26.40; 90.30] |
| Day 5 | [31.10; 90.00] | [4.58; 14.70] | [5.84; 11.55] | [456.0; 1300.0] | [10.60; 41.50] |
| Day 30 | [42.20; 119.00] | [3.39; 10.80] | [4.91; 12.00] | [547.0; 1360.0] | [5.00; 412.00] |
| Day 60 | [42.20; 106.00] | [3.62; 11.40] | [4.41; 8.62] | [678.0; 1620.0] | [5.00; 365.00] |
| Day 90 | [34.20; 86.70] | [3.08; 14.40] | [3.33; 7.72] | [585.0; 1510.0] | [5.00; 453.00] |

| Biomarker/Arm | Free Cotinine (ng/mL) SW | Total NNAL (pg/mL) CC | Total NNAL (pg/mL) SA | Total NNAL (pg/mL) SW |
|---|---|---|---|---|
| Baseline | [547.5; 1210.0] | [46.60; 109.00] | [28.00; 105.00] | [38.45; 98.25] |
| Day −1 | [569.5; 1335.0] | [45.50; 145.00] | [28.20; 131.00] | [47.95; 119.00] |
| Day 0 | [547.5; 1210.0] | [46.60; 109.00] | [28.00; 105.00] | [38.45; 98.25] |
| Day 1 | [570.5; 1280.0] | [52.40; 128.00] | [25.70; 106.00] | [34.90; 83.50] |
| Day 2 | [546.0; 1160.0] | [39.85; 122.00] | [14.80; 89.30] | [24.85; 54.45] |
| Day 3 | [562.5; 1175.0] | [43.50; 109.00] | [13.10; 63.80] | [22.65; 50.80] |
| Day 4 | [640.0; 1230.0] | [46.20; 122.00] | [12.00; 57.70] | [24.75; 54.05] |
| Day 5 | [652.5; 1115.0] | [37.70; 115.00] | [9.12; 45.60] | [17.30; 40.85] |
| Day 30 | [829.0; 1600.0] | [33.30; 132.00] | [8.92; 29.60] | [15.30; 37.00] |
| Day 60 | [730.0; 1560.0] | [44.90; 124.00] | [5.30; 27.90] | [13.70; 30.70] |
| Day 90 | [729.0; 1540.0] | [39.30; 107.00] | [2.50; 31.20] | [9.90; 29.40] |

The invention claimed is:

1. A device for determining the smoking status of a subject and configured to detect the presence of only two or three tobacco smoke exposure biomarkers, wherein said device comprises a plurality of different specific binding agents deposited onto a solid phase to detect the presence of only the two or three tobacco smoke exposure biomarkers in a biological sample, said tobacco smoke exposure biomarkers consisting of:
   (i) cotinine and total 4-(methylnitrosamino)-1-(3-pyridyl)-1-butanol (NNAL); or
   (ii) cotinine and N-acetyl-S[2-carboxyethyl]-L-cysteine (CEMA); or
   (iii) cotinine and total NNAL and CEMA,
   wherein said device is capable of distinguishing current smokers of conventional cigarettes from those who have switched to a smoke-free alternative in which tobacco is heated rather than combusted or from those who have abstained from smoking and providing an indication of the smoking status of the subject based on the distinction.

2. The device according to claim 1, wherein the device is a portable lateral flow immunoassay device configured to perform a competitive immunoassay.

3. The device according to claim 2, wherein the portable lateral flow immunoassay device comprises: (i) a sample pad; (ii) a conjugate pad; and (iii) at least one detection zone.

4. The device according to claim 3, wherein the conjugate pad comprises or consists of labelled specific binding agents each capable of individually binding: (i) cotinine and total NNAL; or (ii) cotinine and CEMA; or (iii) cotinine and total NNAL and CEMA.

5. The device according to claim 3, wherein:
   (a) the conjugate pad comprises or consists of labeled specific binding agents deposited thereon each capable of individually binding: (i) cotinine and total NNAL; or (ii) cotinine and CEMA; or (iii) cotinine and total NNAL and CEMA, and capable of forming labeled specific binding agent conjugates therewith; and
   (b) the at least one detection zone comprises or consists of immobilised specific binding agents each capable of individually binding to (i) cotinine and total NNAL; or (ii) cotinine and CEMA; or (iii) cotinine and total NNAL and CEMA.

6. The device according to claim 3, wherein:
   (a) the conjugate pad comprises or consists of: (i) labelled cotinine or an analogue thereof and labelled total NNAL or an analogue thereof deposited thereon; or (ii) labelled cotinine or an analogue thereof and labelled CEMA or an analogue thereof deposited thereon; or (iii) labelled cotinine or an analogue thereof and labelled total NNAL or an analogue thereof and labelled CEMA or an analogue thereof deposited thereon; and
   (b) the at least one detection zone comprises or consists of immobilised specific binding agents each capable of individually binding: (i) the labelled cotinine or the analogue thereof and the labelled total NNAL or the analogue thereof and cotinine and total NNAL that may be present in a sample; or (ii) the labelled cotinine or the analogue thereof and the labelled CEMA or the analogue thereof and cotinine and CEMA that may be present in a sample; or (iii) the labelled cotinine or the analogue thereof and the labelled total NNAL or the analogue thereof and the labelled CEMA or the analogue thereof and cotinine and total NNAL and CEMA that may be present in a sample.

7. The device according to claim 4, wherein the specific binding agents are labelled with coloured particles.

8. The device according to claim 3, wherein the threshold is: (i) greater than or equal to about 200 ng/ml for 24 hour urinary cotinine and greater than or equal to about 10 pg/ml for total NNAL in 24 hour urine or greater than or equal to about 5 ng/ml for 24 hour urinary CEMA; or (ii) greater than or equal to about 200 ng/ml for 24 hour urinary cotinine and greater than or equal to about 10 pg/ml for total NNAL in 24 hour urine and greater than or equal to about 5 ng/ml for 24 hour urinary CEMA.

9. The device according to claim 1, wherein amounts of the plurality of different specific binding agents are adapted to detect: (i) 24 hour urinary cotinine in an amount of between about 200-800 ng/ml; or (ii) 24 hour urinary total NNAL in 24 hour-urine in an amount of between about 10-125 pg/ml; or (iii) 24 hour urinary CEMA in an amount of between about 5-80 ng/ml; or (iv) a combination of at least two of (i), (ii), and (iii).

10. The device according to claim 8, wherein
   (i) the device is configured to provide a visible indication of cotinine and total NNAL and CEMA on a test line(s) to indicate that the threshold of detection has not been crossed and is indicative of a smoking abstainer;
   (ii) the device is configured to provide no visible indication of cotinine on a test line to indicate that the threshold of detection has been crossed and to provide visible indication of total NNAL and CEMA on a test line to indicate that the threshold of detection has not been crossed and is indicative of a subject exposed to heated tobacco; and
   (iii) the device is configured to provide no visible indication of cotinine and total NNAL on a test line to indicate that the threshold of detection has been crossed and to provide visible detection of CEMA on a test line of a device to indicate that the threshold of detection has not been crossed or to provide no visible indication of cotinine and total NNAL and CEMA on a test line to indicate that the threshold of detection has been crossed and is indicative of a subject exposed to combusted tobacco.

11. A system for determining the smoking status of a subject comprising:
   (a) the device according to claim 1;
   (b) a receptacle adapted for receiving the device according to claim 1;
   (c) an imaging device adapted to acquire at least one digital image of the device according to claim 1; and
   (d) a processor adapted to process the at least one digital image.

12. A system comprising:
   (a) the device according to claim 1;
   (b) a computer data repository operatively coupled to the device, the data repository comprising or consisting of a reference or baseline value of the quantity of biomarkers consisting of cotinine and one or more of total NNAL and CEMA, said reference or baseline values representing a known quantity of biomarker for determining the smoking status of a subject; and
   (c) a computer system programmed to access the data repository and to use information from the data repository in combination with information on the quantity of cotinine and one or more of total NNAL and CEMA in the sample from a subject, to make a determination of the smoking status of the subject,
   wherein said system is capable of distinguishing current smokers of conventional cigarettes from those who have switched to a smoke-free alternative in which tobacco is heated rather than combusted or from those who have abstained from smoking.

13. A kit comprising the device according to claim 1.

14. The device according to claim 3, wherein a predetermined amount of immobilised specific binding agent(s) is present in the detection zone that is capable of forming a signal once the level of the tobacco smoke exposure biomarker(s) in the sample is higher than a predetermined threshold.

15. The device according to claim 4, wherein the labelled specific binding agents is an antibody or fragment thereof, an aptamer, a photoaptamer, an affimer, a protein, a peptide, a peptidomimetic or a small molecule.

* * * * *